(12) United States Patent
Pham et al.

(10) Patent No.: US 9,920,385 B2
(45) Date of Patent: Mar. 20, 2018

(54) **DETECTION OF ECHINOCANDIN-RESISTANT *CANDIDA GLABRATA***

(71) Applicant: THE UNITED STATES OF AMERICA, as represented by the Secretary, Department of Health and Human Services, Washington, DC (US)

(72) Inventors: Cau Dinh Pham, Moorpark, CA (US); Shawn Robert Lockhart, Lilburm, GA (US)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 234 days.

(21) Appl. No.: 14/875,599

(22) Filed: Oct. 5, 2015

(65) Prior Publication Data

US 2016/0102369 A1    Apr. 14, 2016

Related U.S. Application Data

(60) Provisional application No. 62/062,090, filed on Oct. 9, 2014.

(51) Int. Cl.
 *C12Q 1/68* (2018.01)
(52) U.S. Cl.
 CPC ..... *C12Q 1/6895* (2013.01); *C12Q 2600/156* (2013.01); *C12Q 2600/158* (2013.01)

(58) Field of Classification Search
 CPC ............ C12Q 1/6895; C12Q 2600/156; C12Q 2600/158
 USPC ........................................................ 435/91.2
 See application file for complete search history.

(56) References Cited

U.S. PATENT DOCUMENTS

2010/0075302 A1    3/2010  Perlin et al.

OTHER PUBLICATIONS

Das et al., FEMS Immunol. Med. Microbiol. vol. 46, pp. 244-250, 2006.*
Alexander et al., "Increasing Echinocandin Resistance in *Candida glabrata*: Clinical Failure Correlates With Presence of FKS Mutations and Elevated Minimum Inhibitory Concentrations," *CID* 56:1724-1732 (Jun. 15, 2013).
Pham et al., "Development of a Luminex-Based Multiplex Assay for Detection of Mutations Conferring Resistance to Echinocandins in *Candida glabrata*," *Journal of Clinical Microbiology* 52(3):790-795 (Mar. 2014).

* cited by examiner

*Primary Examiner* — Cynthia B Wilder
(74) *Attorney, Agent, or Firm* — Klarquist Sparkman, LLP

(57) ABSTRACT

Probes and primers are disclosed for detecting a *C. glabrata* resistant to an echinocandin in a sample. Method are also disclosed that utilize these probes and primers, wherein the methods can be used to detect a *C. glabrata* resistant to an echinocandin in a sample.

25 Claims, 2 Drawing Sheets

FKS1-HS1

|  | 625 | 626 | 627 | 628 | 629 | 630 | 631 | 632 | 633 |
|---|---|---|---|---|---|---|---|---|---|
|  | F | L | I | L | S | L | R | D | P |

5'- GAA TCA TAC TAC TTC TTG ATT CTA TCT CTA AGA GAT CCA ATCA-3'

| SmC | GAA TCA TAC TAC TTC TTG AT |
| SmT | GAA TCA TAC TAC TTT TTG AT |
| WT1 | T CTA TCT CTA AGA GAT CCA AT |
| 629P | TTG ATT CTA CCT CTA AGA GA |
| 631G | TA TCT CTA GGA GAT CCA AT |
| 632V | T CTA TCT CTA AGA GTT CCA T |

FIG. 1

FKS2-HS1

|     | 659 | 660 | 661 | 662 | 663 | 664 | 665 | 666 | 667 |
|-----|-----|-----|-----|-----|-----|-----|-----|-----|-----|
|     | F   | L   | I   | L   | S   | L   | R   | D   | P   |

| | | |
|---|---|---|
| WT1 | TCG TAC TTC TTC TTG ATT TTG TCT CTA AGA GAC CCT ATC AG | |
| 659Y | TCG TAC TTC TAC TTG ATT TT | |
| 659S | TCG TAC TTC TCC TTG ATT TT | |
| 663P | | TTG ATT TTG CCT CTA AGA GA |
| 663F | | TTG ATT TTG TTT CTA AGA GA |
| WT2 | | TCT CTA AGA GAC CCT ATC A |
| 665G | | TCT CTA GGA GAC CCT ATC A |
| 666V | | TCT CTA AGA GTC CCT ATC AG |
| 667H | | TCT CTA AGA GAC CAT ATC AG |

FIG. 2

DETECTION OF ECHINOCANDIN-RESISTANT *CANDIDA GLABRATA*

CROSS REFERENCE TO RELATED APPLICATIONS

This claims the benefit of U.S. Application No. 62/062,090, filed Oct. 9, 2014, which is incorporated by reference herein.

FIELD OF THE DISCLOSURE

This relates to the field of detection of drug resistance, specifically to the use of polymerase chain reaction (PCR) to determine if *Candida glabrata* in a sample is resistant to an echinocandin.

BACKGROUND

*Candida glabrata* is the second most frequent cause of invasive candidiasis in the United States (Lockhart et al., 2012, J. Clin. Microbiol. 50:3435-3442; Pfaller et al., 2011, J. Clin. Microbiol. 49:396-399). With a large proportion of isolates resistant to fluconazole, echinocandins are the treatment of choice recommended by the Infectious Disease Society of America for candidemia caused by *C. glabrata* (Pappas et al., 2009; Clin Infect Dis. 48(5):503-35). However, as has happened with fluconazole, increased usage of echinocandins has demonstrated the ability of *C. glabrata* to occasionally develop resistance (Pfaller et al., 2009, J Clin Microbiol. 47(10):3185-90; Lee et al., 2009, Arch Intern Med. 169(4):379-83; Pfaller et al., 2012, J Clin Microbiol. 50(4):1199-203; Cleary et al., 2008, Antimicrob Agents Chemother. 54(12):5042-7; Zimbeck et al., 2010, Antimicrob Agents Chemother. 54(12):5042-7; Shields et al., 2012, Antimicrob Agents Chemother. 56(9):4862-9; Alexander et al., 2013, Clin Infect Dis. 56(12):1724-32). With echinocandins recommended for use as empiric therapy for *C. glabrata* infection in US hospitals, rapid identification of isolates which may be echinocandin resistant has increasing clinical relevancy. A need remains for methods that can rapidly determine if a *C. glabrata* in a sample is resistant to echinocandins.

SUMMARY OF THE DISCLOSURE

Probes and primers are disclosed herein for detecting FKS1-hot spot 1 (HS1) DNA or FKS2-HS1 DNA. These probes and primers can be used to detect *C. glabrata* resistant to an echinocandin in a sample. The probes and primers can be labeled. Kits are provided that include these probes and primers.

Methods are disclosed herein for detecting a *C. glabrata* resistant to an echinocandin in a sample. The methods include contacting a biological sample including DNA with unequal amounts of a forward primer and a reverse primer that can be used to amplify a FKS1-HS1 nucleic acid and unequal amounts of a forward and a reverse primer that can be used to amplify a FKS2-HS1 nucleic acid and performing asymmetric polymerase chain reaction (PCR) to form amplified DNA product. The amplified DNA product is then contacted with a set of probes, wherein each probe in the set of probes specifically binds a FKS1-HS1 DNA mutation or specifically binds a FKS2-HS1 DNA mutation, wherein each of the probes is labeled with a unique label such that the identity of each probe is known by detecting the label. Amplified DNA product hybridizes to the set of probes and it is determined if a probe in the set of probes specific for the FKS1-HS1 DNA mutation or a probe in the set of probes specific for an FKS2-HS1 DNA mutation is bound to the amplified DNA product, wherein binding of the probe specific for the FKS1-HS1 DNA or the probe specific for an FKS2-HS1 DNA mutation indicates that the *C. glabrata* is resistant to the echinocandin is present in the sample.

The foregoing and other features and advantages of the invention will become more apparent from the following detailed description of several embodiments which proceeds with reference to the accompanying figures.

BRIEF DESCRIPTION OF THE FIGURES

FIG. 1 is a schematic diagram of the FKS1-HS1 region and the corresponding probes designed to detect them. The amino acids comprising the hotspot region are shown boxed directly above the corresponding codon. Nucleotides encoding mutations detected in this assay are shown in bold. The following sequences are shown: nucleotide 1861 to 1903 of FKS1-HS1 (nucleotide 96-136 of SEQ ID NO: 1) and the corresponding amino acid sequence (SEQ ID NO: 22); SmC (SEQ ID NO: 3); SmT (SEQ ID NO: 4); WT1 (SEQ ID NO: 19); 629P (SEQ ID NO: 5); 631G (SEQ ID NO: 6); and 632V (SEQ ID NO: 7).

FIG. 2 is a schematic diagram of the FKS2-HS1 region and the corresponding probes designed to detect them. The amino acids comprising the hotspot region are shown boxed directly above the corresponding codon. Nucleotides encoding mutations detected in this assay are shown in bold. The following sequences are shown: nucleotide 1965 to 2006 of FKS2-HS1 (83 to 123 of SEQ ID NO: 2) and the corresponding amino acid sequence (SEQ ID NO: 22); WT1 (SEQ ID NO: 20); 659Y (SEQ ID NO: 8); 659S (SEQ ID NO: 9); 663P (SEQ ID NO: 10); 663F (SEQ ID NO: 11); WT2 (SEQ ID NO: 21); 665G (SEQ ID NO: 12); 666V (SEQ ID NO: 13); and 667H (SEQ ID NO: 14).

SEQUENCE LISTING

The nucleic and amino acid sequences provided herein are shown using standard letter abbreviations for nucleotide bases, and three letter code for amino acids, as defined in 37 C.F.R. 1.822.

The Sequence Listing is submitted as an ASCII text file 4239-93148-02_Sequence_Listing.txt, Oct. 5, 2015, 4.49 KB], which is incorporated by reference herein.

SEQ ID NO: 1 is a nucleic acid sequence of the wild type FKS1-HS1 region.

SEQ ID NO: 2 is a nucleic acid sequence of the wild type FKS2-HS1 region.

SEQ ID NOs: 3 is a nucleic acid sequence of a probe that specifically binds a smC FKS1-HS1 region.

SEQ ID NO: 4 is a nucleic acid sequence of a probe that specifically binds a smT FSK1-HS1 region.

SEQ ID NOs: 5-7 are nucleic acid sequences of probes that specifically bind a mutated FKS1-HS1 region that confers echinocandin resistance.

SEQ ID NOs: 8-14 are nucleic acid sequences of probes that specifically bind a mutated FKS2-HS1 region that confer echinocandin resistance.

SEQ ID NOs: 15 and 16 are nucleic acid sequences of primers that can be used to amplify FKS1-HS1.

SEQ ID NOs: 17 and 18 are nucleic acid sequences of primers that can be used to amplify FSK2-HS1.

SEQ ID NO: 19 is the nucleic acid sequence of a probe that specifically binds a wild-type FKS1-HS1 region.

SEQ ID NOs: 20-21 are the nucleic acid sequence of a probe that specifically binds a wild-type FKS2-HS1 region.

SEQ ID NO: 22 is the amino acid sequence encoded by wild-type FKS1-HS1 and FKS2-HS1.

DETAILED DESCRIPTION OF SEVERAL EMBODIMENTS

Echinocandins alter the integrity of the fungal cell wall by inhibiting the activity of the β-1,3-glucan synthase (Park et al., 2005, Antimicrob Agents Chemother. 49(8):3264-73.; Katiyar et al., 2012; Antimicrob Agents Chemother. 56(12): 6304-9). Resistance to echinocandins in *C. glabrata* is caused by amino acid mutations in the hotspot-1 (HS1) region of the Fks1 and Fks2 proteins, which encode β-1,3-glucan synthase subunits. Mutations in Fks1-HS1 and Fks2-HS1 domains that attenuate the susceptibility to echinocandins have been identified. Isolates with the amino acid substitutions S629P, R631G, and D632V/G/E/Y in Fks1-HS1 and F659Y/S, S663P/F, R665G, D666V/G/E, and P667H/T in Fks2-HS1 display elevated in vitro MIC values for echinocandins (Zimbek et al., 2010, Antimicrob Agents Chemother. 54(12):5042-7; Garcia-Effron, 2009, Antimicrob Agents Chemother. 53(9):3690-9.). Moreover, patients who harbor isolates with one or more of these mutations generally fail echinocandin therapy (Cleary et al., 2008, Antimicrob Agents Chemother. 52(6):2263-5; Shields et al., 2012, Antimicrob Agents Chemother. 56(9):4862-9; Garcia-Effron et al., 2010, Antimicrob. Agents Chemother. 54:2225-2227).

DNA sequencing has been the only technique available for identification of mutations in 1-3-β glucan synthase FKS1 and FKS2. Although it is informative and accurate, DNA sequencing is also costly and time consuming. Microsphere-based technology is an alternative to DNA sequencing. This technology can be used for species identification in molds and yeasts (Bovers et al., 2007, J Clin Microbiol. 45(6):1874-83; Etienne et al., 2009, J Clin Microbiol. 47(4): 1096-100; Deak et al., 2010, Can J Microbiol. 56(4):348-51; Babady et al., 2011, J Clin Microbiol. 49(11):3777-82; Balada-Llasat et al., 2012; J Clin Microbiol. 50(2):492-4) and for the identification of single nucleotide polymorphisms (SNPs) (Bando et al., 2012, BMC Cancer. 13(1):405; Thierry et al., 2013, J Microbiol Methods. 95(3):357-365).

The identification of SNPs in the FKS1-HS1 and FKS2-HS1 domains of *C. glabrata*, which confer in vitro resistance to the echinocandins, using microsphere-based technology is disclosed herein. Probes were developed to detect 11 known mutations in FKS1-HS1 and FKS2-HS1. Probes were also developed to detect wild type sequences at these domains. In addition, a lack of binding to the wild-type probes allows identification of new mutations. For example, they can be detected by a lock of binding to the wild type probes and sequencing.

TERMS

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008. As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments, the following explanations of terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Administration: To provide or give a subject an agent, for example, a composition that includes an echinocandin, by any effective route. Exemplary routes of administration for agents include, but are not limited to, oral, injection (such as subcutaneous, intramuscular, intradermal, intraperitoneal, and intravenous), sublingual, transdermal (e.g., topical), intranasal and inhalation routes.

Agent: Any substance or any combination of substances that is useful for achieving an end or result; for example, a substance or combination of substances useful for treating a *C. glabrata* infection in a subject. Agents include effector molecules and detectable markers. Thus, an agent can also be used for detecting nucleic acids in a sample. The skilled artisan will understand that particular agents may be useful to achieve more than one result.

Amplification: A technique that increases the number of copies of a nucleic acid molecule (such as an RNA or DNA). An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. The reaction product can be quantified.

Other examples of amplification include quantitative real-time polymerase chain reaction (qPCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences in a single reaction.

Asymmetric PCR: A PCR reaction that preferentially amplifies one strand of the target DNA. In some embodiments, thermocycling is carried out as in PCR, but with a limiting amount (or leaving out) one of the primers. When the limiting primer becomes depleted, replication increases arithmetically through extension of the excess primer. A modification of this process, named Linear-After-The-Exponential-PCR (or LATE-PCR), uses a limiting primer with a higher melting temperature ($T_m$) than the excess primer to maintain reaction efficiency as the limiting primer concentration decreases mid-reaction.

Biological sample: A sample of biological material obtained from a subject. Biological samples include all clinical samples useful for detection of disease or infection (e.g., a *C. glabrata* infection) in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, cerebrospinal fluid (CSF), etc.), tissue biopsies or autopsies, fine-needle aspirates, and/or tissue sections. In a particular example, a biological sample is obtained from a subject having, suspected of having or at risk of having, a *C. glabrata* infection; for example, a subject having HIV infection, a urogenital infection, or an elderly patient.

*Candida glabrata* (*C. glabrata*): A haploid yeast of the genus *Candida*, previously known as *Torulopsis glabrata*. This species of yeast is non-dimorphic. *C. glabrata* is a highly opportunistic pathogen of the urogenital tract and of the bloodstream. It is prevalent in subjects that are infected with a human immunodeficiency virus, and the elderly. Diagnosis of an infection with *C. glabrata* can be made by culture. Fluconazole, amphotericin B, nystatin, and echinocandins can be used for treating infections with this organism.

Conservative variant: A "conservative variant" of a probe or primer includes sequences that have altered nucleic acid sequences, but retain their ability to bind to the target sequences (and identify or amplify the target sequence) with sufficient specificity. In some particular examples, no more than about 1, 2, 5, or 10 nucleic acids are changed, or the probe or primer retains at least 80%, 85%, 90%, or 95% sequence identity to the original sequence. Conservative variants also include probe or primer sequences to which additional sequence has been added, while still retaining the noted specificity of the probe or primer.

Consists of or consists essentially of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Contacting: Placement in direct physical association, for example solid, liquid or gaseous forms. Contacting includes, for example, direct physical association of fully- and partially-solvated molecules.

Control: A sample or standard used for comparison with an experimental sample. In some embodiments, the control is a negative control sample obtained from a healthy patient or a subject not infected with *C. glabrata*. In some embodiments, the control is a positive control sample including *C. glabrata* nucleic acid. In other embodiments, the positive control is a biological sample obtained from a patient diagnosed with an infection with *C. glabrata*. In still other embodiments, the control is a historical control or standard reference value or range of values (such as a previously tested control sample, such as a group of patients with known not to be infected with *C. glabrata*, or group of samples that represent baseline or normal values.

Detecting: To identify the existence, presence, or fact of something. General methods of detecting are known to the skilled artisan and may be supplemented with the protocols and reagents disclosed herein. For example, included herein are methods of detecting a *C. glabrata* in a biological sample, and determining if the *C. glabrata* is (or is not) resistant to an echinocandin. Detection can include a physical readout, such as fluorescence or a reaction output.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Echinocandin: An antifungal drug that inhibits the synthesis of glucan in the cell wall by inhibiting the enzyme 1-3-β glucan synthase. In some embodiments, an echinocandin is a semisynthetic pneumocandins, which are chemically lipopeptide in nature, consisting of large cyclic (hexa) peptides linked to a long-chain fatty acid. Examples are, caspofungin, micafungin and anidulafungin.

1-3-β glucan synthase and FKS: 1-3-β glucan synthetase is a glucosyltransferase enzyme involved in the generation of beta-glucan in fungi. It is the target of echinocandins. Decreased susceptibility to the echinocandins is associated with mutations in the FKS1 and FKS2 subunits of the 1,3-β-d-glucan synthase complex, which is necessary for the production of 1,3-β-d-glucan. Generally, the mutations occur in two regions, of nine and eight amino acids, designated hot spot 1 (HS1) that appear in both FKS1 and FKS2, respectively. These mutations in the FKS1 and FKS2 genes result in the inability of echinocandins to inhibit the production of 1,3-β-d-glucan (see Zimbeck et al., 2010, Antibmicrob. Agents Chemother. 54(12): 5042-7).

Hybridization: The terms "annealing" and "hybridization" refer to the formation of base pairs between complementary regions of DNA, RNA, or between DNA and RNA of nucleic acids. Examples of annealing and hybridization include formation of base pairs between two separate nucleic acid molecules, as well as formation of base pairs between nucleic acids on a single nucleic acid molecule.

In some examples, hybridization is between two complementary nucleic acid sequences, for example nucleic acid sequences that are at least 90% complementary to each other, such as at least 91%, 92%, 93%, 94%, 95%, 96%, 97%, 98%, 99%, or 100% complementary to each other.

In additional embodiments, hybridization conditions resulting in particular degrees of stringency and specificity will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Identity)
Hybridization: 6×SSC at RT to 55° C. for 16-20 hours
Wash at least twice: 2×-3×SSC at RT to 55° C. for 20-30 minutes each.

In some embodiments, the probes and primers disclosed herein can hybridize to nucleic acid molecules under low stringency, high stringency, and very high stringency conditions.

Inhibiting or treating an infection: Inhibiting the full development of an infection such as with *C. glabrata*. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the infection in a susceptible subject, a reduction in severity of some or all clinical symptoms of the infection, a slower progression of the infection, a reduction in fungal titer, an improvement in the overall health or well-being of the subject, or by other parameters well known in the art that are specific to the particular condition. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid molecule or protein) has been substantially separated or purified away from other biological components in the cell of the organism in which the component naturally occurs. The term "isolated" does not require absolute purity. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Label: A detectable molecule that is conjugated directly or indirectly to a second molecule, such as a nucleic acid molecule, to facilitate detection of the second molecule. The person of ordinary skill in the art is familiar with detectable markers for labeling nucleic acid molecules and their use. In some examples, the detectable marker can be capable of detection by ELISA, spectrophotometry, flow cytometry, or microscopy. Specific, non-limiting examples of detectable markers include fluorophores, fluorescent proteins, chemiluminescent agents, enzymatic linkages, radioactive isotopes and heavy metals or compounds. In several embodiments, the detectable markers are designed for use with qPCR, such as multiplex qPCR. Various methods of labeling nucleic acid molecules are known in the art and may be used. A "unique" label is a label that is distinct from others in a reaction, such that the identity of a single bound molecule can be known when the label is detected.

Multiplex qPCR: Amplification and detection of multiple nucleic acid species in a single qPCR reaction. By multiplexing, target nucleic acids can be amplified in single tube. In some examples, multiplex PCR permits the simultaneous detection of the amplification products of a region of the FKS gene of *C. glabrata* using the disclosed probes.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen.

Oligonucleotide probes and primers: A probe includes an isolated nucleic acid (usually of 100 or fewer nucleotide residues) attached to a detectable label or reporter molecule, which is used to detect a complementary target nucleic acid molecule by hybridization and detection of the label or reporter. Isolated oligonucleotide probes (which as defined herein also include the complementary sequence and corresponding RNA sequences) are of use for detection of FKS mutations in *C. glabrata*. Typically, probes are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length. For example, a probe can be about 10-100 nucleotides in length, such as, 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50 or 25-80 nucleotides in length.

Primers are nucleic acid molecules, usually DNA oligonucleotides of about 10-50 nucleotides in length (longer lengths are also possible). Typically, primers are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. For example, a primer can be about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length.

Probes and primers can also be of a maximum length, for example no more than 15, 25, 25, 40, 50, 75 or 100 nucleotides in length.

Primers may be annealed to a complementary target DNA strand by nucleic acid hybridization to form a hybrid between the primer and the target DNA strand, and then extended along the target DNA strand by a DNA polymerase enzyme. One of skill in the art will appreciate that the hybridization specificity of a particular probe or primer typically increases with its length. Thus, for example, a probe or primer including 20 consecutive nucleotides typically will anneal to a target with a higher specificity than a corresponding probe or primer of only 15 nucleotides. In some embodiments, probes and primers are used in combination in a quantitative PCR reaction.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Additionally, an intron is operably linked to an exon for the function of splicing. Generally, operably linked nucleotide sequences are contiguous.

Primer pair: Two primers (one "forward" and one "reverse") that can be used for amplification of a nucleic acid sequence, for example by polymerase chain reaction (PCR) or other in vitro nucleic-acid amplification methods. The forward and reverse primers of a primer pair do not hybridize to overlapping complementary sequences on the target nucleic acid sequence.

Quantitative real-time PCR (qPCR): A method for detecting and measuring products generated during each cycle of a PCR, which are proportionate to the amount of template nucleic acid prior to the start of PCR. The information obtained, such as an amplification curve, can be used to determine the presence of a target nucleic acid (such as a *C. glabrata* nucleic acid) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999); *PCR Protocols* (Academic Press, New York, 1989); *A-Z of Quantitative PCR*, Bustin (ed.), International University Line, La Jolla, Calif., 2004; and *Quantitative Real-Time PCR in Applied Microbiology*, Filion (Ed), Caister Academic Press, 2012.

In some examples, the amount of amplified target nucleic acid (for example a *C. glabrata* nucleic acid) is detected using a labeled probe, such as a probe labeled with a fluorophore. In this example, the increase in fluorescence emission is measured in real-time, during the course of the real-time PCR. This increase in fluorescence emission is directly related to the increase in target nucleic acid amplification. In some examples, the change in fluorescence (Delta Rn; dRn; ΔRn) is calculated using the equation dRn=$Rn^+$−$Rn^-$, with $Rn^+$ being the fluorescence emission of the product at each time point and $Rn^-$ being the fluorescence emission of the baseline. The dRn values are plotted against cycle number, resulting in amplification plots for each sample. The threshold value ($C_t$) is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$, for example. The efficiency of the PCR should be 90-100% meaning doubling of the amplicon at each cycle. This corresponds to a slope of −3.1 to −3.6 in the $C_t$ vs. log-template amount standard curve.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sensitivity and specificity: Statistical measurements of the performance of a binary classification test. Sensitivity measures the proportion of actual positives which are correctly identified (e.g., the percentage of samples that are identified as including nucleic acid from a particular pathogen). Specificity measures the proportion of negatives which are correctly identified (e.g., the percentage of samples that are identified as not including nucleic acid from a particular pathogen).

Sequence identity: The similarity between two nucleic acid sequences, is expressed in terms of the similarity between the sequences, otherwise referred to as sequence identity. Sequence identity is frequently measured in terms of percentage identity, similarity, or homology; a higher percentage identity indicates a higher degree of sequence similarity.

The NCBI Basic Local Alignment Search Tool (BLAST), Altschul et al., *J. Mol. Biol.* 215:403-10, 1990, is available from several sources, including the National Center for Biotechnology Information (NCBI, Bethesda, Md.), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al.; and Tijssen, *Hybridization With Nucleic Acid Probes, Part I: Theory and Nucleic Acid Preparation*, Laboratory Techniques in Biochemistry and Molecular Biology, Elsevier Science Ltd., 1993.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Specifically binds: A nucleic acid sequence that, under a defined set of reaction conditions, binds to its complement and not to other nucleic acid sequences. A probe that specifically binds to its target can be used in RT-PCR assays. Generally a probe that specifically binds one FKS1-HS1 mutations can be used to distinguish that nucleic acid sequence from other FKS1-HS1 mutations, from wild-type FKS1-HS1 nucleic acids, and from FKS2-HS1 nucleic acids. Similarly, a probe that specifically binds one FKS2-HS1 mutations can be used to distinguish that nucleic acid sequence from other FKS2-HS1 mutations, from wild-type FKS2-HS1 nucleic acids, and from FKS1-HS1 nucleic acids.

Subject: Any mammal, such as humans, non-human primates, pigs, sheep, cows, rodents and the like. In two non-limiting examples, a subject is a human subject or a murine subject. Thus, the term "subject" includes both human and veterinary subjects. An immunocompromised subject is a subject with a suppressed immune system, such as a subject with HIV.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. In some examples, a target nucleic acid includes a region of the FKS1 or FKS2 regions of *C. glabrata*. Purification or isolation of the target nucleic acid molecule, if needed, can be conducted by methods known to those in the art, such as by using a commercially available purification kit or the like.

Therapeutically effective amount: The amount of an agent (such as an anti-echinocandin) that alone, or together with one or more additional agents, induces the desired response, such as, for example treatment of a *C. glabrata* infection in a subject. Ideally, a therapeutically effective amount provides a therapeutic effect without causing a substantial cytotoxic effect in the subject.

Several preparations disclosed herein are administered in therapeutically effective amounts. A therapeutically effective amount of an echinocandin that is administered to a human or veterinary subject will vary depending upon a number of factors associated with that subject, for example the overall health of the subject. A therapeutically effective amount of the agents can be determined by varying the dosage and measuring the resulting therapeutic response, such as the reduction of symptoms associated with a *C. glabrata* infection, or a decrease in the fungal titer. The disclosed agents can be administered in a single dose, or in several doses, as needed to obtain the desired response. However, the therapeutically effective amount of can be dependent on the source applied, the subject being treated, the severity and type of the condition being treated, and the manner of administration.

Under conditions sufficient for: A phrase that is used to describe any environment that permits a desired activity. In one example the desired activity is amplification of a nucleic acid molecule.

Nucleic Acids and Kits

Several embodiments of the methods disclosed herein include amplifying a nucleic acid molecule including FKS1-HS1 and/or FKS2-HS1 nucleic acid sequence.

The wild type FKS1 gene is 5592 base pairs in length and is provided in GENBANK Accession No. HM366440.1, Jun. 26, 2012, which is incorporated herein by reference. The presently claimed methods amplify the HS1 region, which is from nucleotide 1766 to 1979 of the FKS1 gene. The wild type sequence of this region is provided below:

```
                                         (SEQ ID NO: 1)
CTCAA ACCTTCACTG CCTCCTTTGC ACCTTTGCAT

GGTCTTGACA GATGGTTGTC TTACCTGGTT TGGGTTACTG

TTTTTGCTGC TAAGTACGCT GAATCATACT ACTTCTTGAT

TCTATCTCTA AGAGATCCAA TCAGAATTTT GTCTACCACT

ACCATGAGAT GTACTGGTGA ATACTGGTGG GGTTCAAAGC

TATGTAGACA TCAATCAAA
```

The wild type FKS2 gene nucleic acid sequence is 5694 base pairs in length and is provided in GENBANK® Accession No. HM366442.1, Jun. 26, 2012, which is incorporated herein by reference. The presently claimed methods amplify the FKS2-HS1 region, which is from nucleotide 1884 to 2056 of this gene. The wild type sequence is provided below:

```
                                              (SEQ ID NO: 2)
ATCTTTT GCCCCATTAC AAGGTTTGGA TAGATGGTTA

TCTTATTTAG TTTGGGTTAC AGTTTTTGCT GCCAAATACT

CTGAATCGTA CTTCTTCTTG ATTTTGTCTC TAAGAGACCC

TATCAGAATT TTATCAACTA CTACCATGAG ATGTACTGGT

GAGTATTGGT GGGGTT
```

Mutations in FKS1-HS1 result in resistance of *C. glabrata* to echinocandins. Exemplary mutations in FKS1-HS1 that result in resistance to echinocandins are shown in FIG. 1. These include, but are not limited to, 629P, 631G, and 632V. These include:

a) a probe that specifically binds FKS1-HS1 encoding FKS1 with a 629P mutation including the nucleic acid sequence set forth as SEQ ID NO: 5;

b) a probe that specifically binds FKS1-HS1 encoding FKS1 with a 631G mutation including the nucleic acid sequence set forth as SEQ ID NO: 6; and c) a probe that specifically binds FKS1-HS1 encoding FKS1 with a 632V mutation comprising the nucleic acid sequence set forth as SEQ ID NO: 7.

Mutations in FKS1-HS1 that do not result in resistant to echinocandins are also shown in FIG. 1. These include:

a) a probe that specifically binds FKS1-HS1 DNA encoding FKS1 with a smC mutation including the nucleic acid sequence set forth as SEQ ID NO: 3; and b) a probe that specifically binds FKS1-HS1 encoding FKS1 with a smT mutation including the nucleic acid sequence set forth as SEQ ID NO: 4;

The methods disclosed herein can include the use of probes specific for one or more of mutations in FSK1-HS1. These probes can be, for example, 17 to 30 nucleotides in length, such as 18 to 25 nucleotides in length, such as 18 to 25 nucleotides in length, such as 18, 19, 20, 21, 22, 23, 24, 25, 26, 27, 28, 29 or 30 nucleotides in length.

Thus, probes are provided herein for one or more of a SmC, SmT, 629P, 631G, and 632V mutation. In some embodiments, kits are provided that include these probes, such as 1, 2, 3, 4, or all 5 of these probes. Exemplary probes, as shown in FIG. 1, include:

a) a probe that specifically binds FKS1-HS1 DNA encoding FKS1 with a smC mutation including the nucleic acid sequence set forth as SEQ ID NO: 3;

b) a probe that specifically binds FKS1-HS1 encoding FKS1 with a smT mutation including the nucleic acid sequence set forth as SEQ ID NO: 4;

c) a probe that specifically binds FKS1-HS1 encoding FKS1 with a 629P mutation including the nucleic acid sequence set forth as SEQ ID NO: 5;

d) a probe that specifically binds FKS1-HS1 encoding FKS1 with a 631G mutation including the nucleic acid sequence set forth as SEQ ID NO: 6; and e) a probe that specifically binds FKS1-HS1 encoding FKS1 with a 632V mutation comprising the nucleic acid sequence set forth as SEQ ID NO: 7.

Mutations in FKS2-HS1 also result in resistance of *C. glabrata* to echinocandins. Exemplary mutations in FKS2 that result in resistance to echinocandins are shown in FIG. 2. These include, but are not limited to, 659Y, 659S, 663P, 663F, 665G, 666V, and 667H. These probes can be, for example, 17 to 30 nucleotides in length, such as 18 to 25 nucleotides in length, such as 18 to 25 nucleotides in length, such as 18, 19, 20, 21, 22, 23, 24 or 25 nucleotides in length.

The methods disclosed herein can include the use of probes specific for these mutations. These probes can be, for example, 17 to 30 nucleotides in length, such as 18 to 25 nucleotides in length, such as 18 to 25 nucleotides in length, such as 18, 19, 20, 21, 22, 23, 24, 25, 26, 27, 28 29 or 30 nucleotides in length. In some embodiments, kits are provided that include these probes, such as 1, 2, 3, 4, 5, 6 or all of these probes. Exemplary probes, as shown in FIG. 2, include:

a) a probe that specifically binds FKS2-HS1 DNA encoding FKS1 with a 659Y mutation including the nucleic acid sequence set forth as SEQ ID NO: 8;

b) a probe that specifically binds FKS2-HS1 encoding FKS1 with a 659S mutation including the nucleic acid sequence set forth as SEQ ID NO: 9;

c) a probe that specifically binds FKS2-HS1 encoding FKS1 with a 663P mutation including the nucleic acid sequence set forth as SEQ ID NO: 10;

d) a probe that specifically binds FKS2-HS1 encoding FKS1 with a 663F mutation including the nucleic acid sequence set forth as SEQ ID NO: 11;

e) a probe that specifically binds FKS2-HS1 encoding FKS1 with a 665G mutation including the nucleic acid sequence set forth as SEQ ID NO: 12;

f) a probe that specifically binds FKS2-HS1 encoding FKS1 with a 666V mutation including the nucleic acid sequence set forth as SEQ ID NO: 13; and g) a probe that specifically binds FKS2-HS1 encoding FKS1 with a 667H mutation including the nucleic acid sequence set forth as SEQ ID NO: 14.

The probes discloses herein can be labeled, as disclosed below.

As disclosed herein, asymmetric PCR can be use amplify an FKS1-HS1 region and/or an FKS2-HS1 region. These primers can be, for example, 17 to 30 nucleotides in length, such as 18 to 26 nucleotides in length or 18 to 24 nucleotides in length, such as 18, 19, 20, 21, 22, 23, 24, 25, or 26 nucleotides in length. Exemplary primers for the FKS1-HS1 region include the nucleic acid sequence set forth as:

```
                                             (SEQ ID NO: 15)
5'-TCA AAC CTT CAC TGC CTC CT-3';
or (SEQ ID NO: 16)
5'-TTT GAT TGA TGT CTA CAT AGC TTT-3'.
```

Exemplary primers for the FKS2-HS1 region include the nucleic acid sequence set forth as:

```
                                             (SEQ ID NO: 17)
5'-TCT TTT GCC CCA TTA CAA GG-3'
or (SEQ ID NO: 18)
5'-AAC CCC ACC AAT ACT CAC CA-3'.
```

Any of the disclosed primers can be labeled or unlabeled, as disclosed below.

The oligonucleotide probes and/or primers and compositions including such probes and/or primers disclosed herein can be supplied in the form of a kit for use in identification of resistant *C. glabrata* in a biological sample. In such a kit, one or more of the oligonucleotide probes and/or primers is provided in one or more containers. An oligonucleotide probe or primer can be provided suspended in an aqueous solution, or as a freeze-dried or lyophilized powder. The container(s) in which the oligonucleotide(s) are supplied can be any conventional container that is capable of holding the supplied form; e.g., microfuge tubes, ampoules, or bottles. In some applications, pairs of primers can be provided in pre-measured single use amounts in individual, typically disposable, tubes or equivalent containers. With such an arrangement, the sample to be tested for the identification of FKS1-HS1 and/or FKS2-HS1 nucleic acids can be added to the individual tubes and amplification carried out directly.

In some embodiments, the kit includes a container including a first oligonucleotide primer pair including a forward oligonucleotide primer and a reverse oligonucleotide primer, wherein the forward oligonucleotide primer and the reverse primer amplify FKS1-HS1. Suitable non-limiting examples are a primer comprising the nucleic acid sequence set forth as SEQ ID NO: 15 and a primer comprising the nucleic acid sequence set forth as SEQ ID NO: 16. The kit can include an oligonucleotide primer pair including a forward oligonucleotide primer and a reverse oligonucleotide primer, wherein the forward and the reverse primer can be used to amplify FKS2-HS1. Suitable non-limiting examples are a primer comprising the nucleic acid sequence set forth as SEQ ID NO: 17 and a primer comprising the nucleic acid sequence set forth as SEQ ID NO: 18. The kit can include both a primer pair that can be used to amplify FKS1-HS1 and FKS2-HS1.

In additional embodiments, the kit can further include one or more containers providing a set of probes for the detection of FKS1-HS1 mutations. Each probe in the set of probes can be labeled with a unique label, as disclosed below. In yet other embodiments, the kit can further one or more containers providing a set of probes for the detection of FKS2-HS1 mutations. Each probe in the set of probes can be labeled with a unique label, as disclosed below. In more embodiments, the kit can further include one or more containers providing two sets of probes, one for the detection of FKS1-HS1 mutations and a second for the detection of FKS2-HS1. Each probe from both sets of probes can be labeled with a unique label, as disclosed below. The primer pairs and the probes can be formulated for use in a multiplex qPCR assay.

In some embodiments, kits can also include the reagents necessary to carry out PCR amplification reactions (including, but not limited to, qPCR reactions). In some examples, the kit can include reagents for DNA sample preparation reagents, appropriate buffers (e.g., polymerase buffer), salts (e.g., magnesium chloride), and deoxyribonucleotides (dNTPs). One or more control sequences for use in the PCR reactions can also be supplied in the kit.

In one embodiment, kits are supplied with instructions. In one specific, non-limiting example, the instructions are written instructions. In another such example, the instructions are provided in electronic format. The instructions may, for example, instruct the user how to use the primers and probes to amplify and detect the nucleic acid sequences using a PCR reaction, and then determine if a sample contains wild-type and/or echinocandin resistant *C. glabrata*.

Methods for Detecting *C. glabrata* that Includes an FKS Mutation

Methods are disclosed for amplifying and detecting a plurality of nucleic acid targets in a sample, wherein the targets are FKS1-HS1 and FKS2-HS1 DNA sequences. Thus, in some embodiments, the methods include detecting the presence (or absence) of *C. glabrata* that is resistant to an echinocandin. The sample can be an environmental sample or a biological sample. Suitable samples include all environmental samples, such as water and soil samples. In some embodiments, the sample can be a biological sample from a subject suspected of having an infection with *C. glabrata* that is suspected of being resistant to an echinocandin. Suitable samples include all clinical samples useful for detection of infection in subjects. Exemplary biological samples include, without limitation, cells, cell lysates, blood smears, cytocentrifuge preparations, cytology smears, bodily fluids (e.g., blood, plasma, serum, saliva, sputum, urine, bronchoalveolar lavage, semen, CSF, vaginal discharge, etc.), tissue biopsies or autopsies, fine-needle aspirates, and/or tissue sections. In one embodiment, the biological sample is a urine sample. In another embodiment, the biological sample is a blood or serum sample. Generally the samples include nucleic acids.

Several embodiments of the method disclosed herein use of PCR and/or qPCR. PCR reaction conditions typically include either two or three step cycles. Two step cycles have a denaturation step followed by a hybridization/elongation step. Three step cycles include a denaturation step followed by a hybridization step during which the primer hybridizes to the strands of DNA, followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended.

Primers are typically designed so that all of the primers participating in a particular reaction have melting temperatures that are within at least five degrees Celsius, and more typically within two degrees Celsius of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 µM to 0.5 µM. As discussed below, primers can be included in unequal amounts, such that one strand, such as a sense or antisense strand, is preferentially amplified, as compared to the other strand, such as the antisense or sense strand, respectively.

In a typical PCR cycle, a sample including a DNA polynucleotide and a PCR reaction cocktail is denatured by treatment in a thermal cycler at about 90-98° C. for 10-90 seconds. The denatured polynucleotide is then hybridized to oligonucleotide primers by treatment in a thermal cycler at a temperature of about 30-65° C. for 0.5-2 minutes. Chain extension then occurs by the action of a DNA polymerase on the polynucleotide annealed to the oligonucleotide primer. This reaction occurs at a temperature of about 68-72° C. for 30 seconds to 5 minutes. Any desired number of PCR cycles may be carried out depending on variables including but not limited to the amount of the initial DNA polynucleotide, the length of the desired product and primer stringency. The above temperature ranges and the other numbers are exemplary and not intended to be limiting. These ranges are dependent on other factors such as the type of enzyme, the type of container or plate, the type of biological sample, the size of samples, etc. One of ordinary skill in the art will recognize that the temperatures, time durations and cycle number can readily be modified as necessary. Exemplary reaction conditions are disclosed in the examples section below.

Any type of thermal cycler apparatus can be used for the amplification of nucleic acids as described above. Examples of suitable apparatuses include PTC-100® Peltier Thermal Cycler (MJ Research, Inc.; San Francisco, Calif.), a ROBOCYCLER® 40 Temperature Cycler (Agilent/Stratagene; Santa Clara, Calif.), or GENEAMP® PCR System 9700 (Applied Biosystems; Foster City, Calif.). For real-time PCR, any type of real-time thermocycler apparatus can be used. For example, ICYCLER IQ™ or CFX96™ real-time detection systems (Bio-Rad, Hercules, Calif.), LIGHTCYCLER® systems (Roche, Mannheim, Germany), a 7700 Sequence Detector (Perkin Elmer/Applied Biosystems; Foster City, Calif.), ABI™ systems such as the 7000, 7300, 7500, 7700, or 7900 systems (Applied Biosystems; Foster City, Calif.), or an MX4000™,MX3000™ or MX3005™ qPCR system (Agilent/Stratagene; Santa Clara, Calif.), DNA ENGINE OPTICON® Continuous Fluorescence Detection System (Bio-Rad, Hercules, Calif.), ROTORGENE® Q real-time cycler (Qiagen, Valencia, Calif.), or SMARTCYCLER® system (Cepheid, Sunnyvale, Calif.) can be used to amplify and detect nucleic acid sequences in real-time. In some embodiments, real-time PCR is performed using a TAQMAN® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus. In additional embodiments, visualization of the PCR reaction, such as in real time, is performed using the LUMINEX® MAGPIX® PCR system, as disclosed below.

An amplification cycle can be performed to form amplification products for each of the FKS1-HS1 and/or FKS2-HS1 nucleic acid sequences. Thus, primers can be included in a reaction, and nucleic acid amplification performed, to amplify FKS1-HS1 and/or FKS2-HS1 nucleic acid sequences from the sample using primer pairs. In some embodiments, the amplification cycle is asymmetric, such that one strand of a double stranded DNA for FKS1-HS1 and/or FKS2-HS1 nucleic acid (e.g., the sense or the antisense strand) is preferentially amplified. This can be achieved, for example, by the presence of unequal amounts of primers, such as a 1:2, 1:3, 1:4, 1:5, 1:6, 1:7, 1:8, 1:9 or 1:10 ratio of the amount of the forward to reverse primer, or 1:2, 1:3, 1:4, 1:5, 1:6, 1:7, 1:8, 1:9 or 1:10 ratio of the amount of the reverse primer to a forward primer.

In some embodiments, the method includes combining a sample comprising FKS1-HS1 and/or FKS2-HS1 nucleic acid targets, primer pairs for priming amplification of the nucleic acid targets. Optionally one or more primers can be labeled. In further embodiments, a plurality of probes complementary to the FKS1-HS1 and/or FKS2-HS1 nucleic acid sequences, such as specific mutations, are also included in the reaction. Optionally, one or more probes that are complementary to wild-type FKS1-HS1 and or FKS2-HS1 nucleic acid sequences are also included in the assay. The probes can be uniquely labeled. In some embodiments, this combination can occur in a chamber.

In certain embodiments, the methods are used for the detection of FKS1-HS1 nucleic acids. Thus, the method can include the use of primers that are, for example, 17 to 30 nucleotides in length, such as 18 to 25 nucleotides, such as 19 to 24 nucleotides in length or 20 to 24 nucleotides in length. In some examples, the one or both primers is 18, 19, 20, 21, 22, 23, 24, or 25 nucleotides in length. Thus, the method can include the use of a primer for the FKS1-HS1 region that includes the nucleic acid sequence set forth as: 5'-TCA AAC CTT CAC TGC CTC CT-3' (SEQ ID NO:15). The method can include the use of a primer for the FKS1-HS1 region that includes the nucleic acid sequence set forth as 5'-TTT GAT TGA TGT CTA CAT AGC TTT-3' (SEQ ID NO: 16). The method can include the use of both the primer comprising SEQ ID NO: 15 and the use of the primer comprising SEQ ID NO: 16. In additional embodiments, the methods can include the use of these primers in an asymmetric PCR reaction to amplify FKS1-HS1 nucleic acids. Optionally, one or both of the primers can be labeled.

In certain embodiments, the methods are used for the detection of FKS2-HS1 nucleic acids. Thus, the method can include primers that are, for example, 17 to 30 nucleotides in length, such as 18 to 26 nucleotides in length or 18 to 24 nucleotides in length, such as 18, 19, 20, 21, 22, 23, 24, 25, or 26 nucleotides in length. [The method can include the use of a primer for the FKS2-HS1 region that includes the nucleic acid sequence set forth as 5'-TCT TTT GCC CCA TTA CAA GG-3'(SEQ ID NO: 17). The method can include the use of a primer for the FKS1-HS1 region that includes the nucleic acid sequence set forth as 5'-AAC CCC ACC AAT ACT CAC CA-3' (SEQ ID NO: 18). The method can include the use of a primer comprising SEQ ID NO: 17 and the use of a primer comprising SEQ ID NO: 18. In additional embodiments, the methods can include the use of these primers in an asymmetric PCR reaction to amplify FKS1-HS1 nucleic acids. Optionally, one or both of the primers can be labeled.

In some embodiments, the methods detect both FKS1-HS1 nucleic acids and FKS2-HS1 nucleic acids. In specific non-limiting examples, the method can include the use of a primer comprising SEQ ID NO: 15, the use of a primer comprising SEQ ID NO: 16, the use of a primer comprising SEQ ID NO: 17, and the use of a primer comprising SEQ ID NO: 17. In additional embodiments, the methods can include the use of these primers in an asymmetric PCR reaction to amplify both FKS1-HS1 and FKS2-HS1 nucleic acids. Optionally, one primer in each primer pair can be labeled, or both primers in each primer pair can be labeled.

The reaction product(s) can be quantitated, such as, but not limited to, using qPCR. qPCR monitors the fluorescence emitted during the reaction as an indicator of amplicon production during each PCR cycle, as opposed to endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. Thus, the procedure follows the general pattern of polymerase chain reaction, but the nucleic acid molecule is quantified after each round of amplification.

Probe based quantitative amplification relies on the sequence-specific detection of a desired amplified product. Unlike the dye-based quantitative methods, it utilizes target-specific probe labeled with a detectable marker such as a base-linked or terminally-linked fluorophore and quencher. Such markers are known to the person of ordinary skill in the art and described herein. Further, methods for performing probe-based quantitative amplification are well established in the art (see, e.g., U.S. Pat. No. 5,210,015). In some embodiments, the fluorescently-labeled DNA probes used to identify amplification products have spectrally distinct emission wavelengths, thus allowing them to be distinguished within the same reaction tube, for example in multiplex PCR, such as a multiplex real-time PCR.

In some embodiments, included in the reaction are (a) at least one probe that specifically binds 629P, 631G or 632V FKS1-HS1 nucleic acids; and/or (b) at least one probe that specifically bind 659Y, 659S, 663P, 663F, 665G, 666V, and/or 667H of FKS2-HS1 nucleic acids. Optionally, at least one probe that specifically binds SmC and/or SmT is also included. In additional embodiments, included in the reaction are (a) 1, 2, 3, 4 or all 5 probes that specifically bind SmC, SmT, 629P, 631G, and/or 632V FKS1-HS1 nucleic acids; and/or (b) 1, 2, 3, 4, 5, 6 or all 7 probes that specifically bind 659Y, 659S, 663P, 663F, 665G, 666V, and/or 667H of FKS2-HS1 nucleic acids.

In specific non-limiting examples, included in the reaction are (a) probes that specifically bind 629P, 631G, and 632V FKS1-HS1 nucleic acids; and/or (b) probes that specifically bind 659Y, 659S, 663P, 663F, 665G, 666V, and 667H FKS2-HS1 nucleic acids. In specific non-limiting examples, included in the reaction are (a) probes that specifically bind SmT, SmC, 629P, 631G, and 632V FKS1-HS1 nucleic acids; and/or (b) probes that specifically bind 659Y, 659S, 663P, 663F, 665G, 666V, and 667H FKS2-HS1 nucleic acids.

One or more probes that specifically bind a wild-type FKS1-HS1 nucleic acid sequence can be included in the reaction. One or more probes that specifically bind a wild-type FKS2-HS1 nucleic acid sequence can be included in the reaction. Thus, in some embodiments, included in the reaction are one or more probes that specifically bind a wild-type FKS1-HS1 nucleic acid and one or more probes that specifically bind a wild-type FKS2-HS1 nucleic acid sequence. These p robes can include the nucleic acid sequence set forth as one of SEQ ID NOs: 19-21.

Any of the probes can be, for example, 18 to 30 nucleotides in length, such as 19 to 30 nucleotides in length, such as 20 to 30 nucleotides in length, or 25 to 30 nucleotides in length. Thus, the probe can be 18, 19, 20, 21, 22, 23, 24, 25, 26, 27, 28, 29 or 30 nucleotides in length.

Probes of use in any of the methods disclosed herein include: a) a probe that specifically binds FKS1-HS1 encoding FKS1 with a 629P mutation including the nucleic acid sequence set forth as SEQ ID NO: 5; b) a probe that specifically binds FKS1-HS1 encoding FKS1 with a 631G mutation including the nucleic acid sequence set forth as SEQ ID NO: 6; and c) a probe that specifically binds FKS1-HS1 encoding FKS1 with a 632V mutation comprising the nucleic acid sequence set forth as SEQ ID NO: 7. Optionally, the method can include the use of a) a probe that specifically binds FKS1-HS1 DNA encoding FKS1 with a SmC mutation including the nucleic acid sequence set forth as SEQ ID NO: 3; and/or b) a probe that specifically binds FKS1-HS1 encoding FKS1 with a SmT mutation including the nucleic acid sequence set forth as SEQ ID NO: 4. These mutations do not confer echinocandin resistance. Optionally, the method can use a probe that specifically binds a wild-type FKS-HS1 nucleic acid, such as a probe comprising the nucleic acid sequence set forth as SEQ ID NO: 19.

Probes of use in any of the methods disclosed herein also include: a) a probe that specifically binds FKS2-HS1 DNA encoding FKS1 with a 659Y mutation including the nucleic acid sequence set forth as SEQ ID NO: 8; b) a probe that specifically binds FKS2-HS1 encoding FKS2 with a 659S mutation including the nucleic acid sequence set forth as SEQ ID NO: 9; c) a probe that specifically binds FKS2-HS1 encoding FKS2 with a 663P mutation including the nucleic acid sequence set forth as SEQ ID NO: 10; d) a probe that specifically binds FKS2-HS1 encoding FKS2 with a 663F mutation including the nucleic acid sequence set forth as SEQ ID NO: 11; e) a probe that specifically binds FKS2-HS1 encoding FKS2 with a 665G mutation including the nucleic acid sequence set forth as SEQ ID NO: 12; f) a probe that specifically binds FKS2-HS1 encoding FKS2 with a 666V mutation including the nucleic acid sequence set forth as SEQ ID NO: 13; and g) a probe that specifically binds FKS2-HS1 encoding FKS2 with a 667H mutation including the nucleic acid sequence set forth as SEQ ID NO: 14. Optionally, the method uses a probe that specifically binds a wild-type FKS2-HS1 nucleic acid. Thus, a probe comprising the nucleic acid sequence set forth as SEQ ID NO: 20, a probe comprising the nucleic acid sequence set forth as SEQ ID NO: 21, or both of these probes can be used.

Each probe included in the reaction can be uniquely labeled. In some embodiments, each of the probes is labeled with a different label, such that the identity of the probe is known from the label. The label can be detected by any means known to those of skill in the art in order to detect the presence of the nucleic acid sequence.

In some embodiments, the probes are immobilized on a plurality of encoded particles such that the identity of each probe is known from the encoded particle on which it is immobilized. Thus, each probe is labeled with a unique encoded particle. The amplification products are hybridized to the probes immobilized on encoded particles. When the reaction is in a chamber, the encoded particles and the amplification products hybridized to the probes immobilized on the encoded particles can then be attracted to the surface of the chamber. A signal from the encoded particles is detected from the amplification products.

In additional embodiments, the encoded particles can be dispersed and the amplification products hybridized to the probes immobilized on the encoded particles from the surface of the chamber prior to performing a further amplification cycle. In some embodiments, the steps are then repeated at least once, such that the nucleic acid targets in the sample are amplified and detected.

In some embodiments, the steps can be repeated between 10 to 40 times, such as 15 to 40 times, such as 20 to 40 times. The steps can be repeated 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 times. In some embodiments, the assay can be a real time assay. However, the assay does not need to be a real time PCR assay.

In one embodiment, the method includes amplifying and detecting a FKS1-HS1 and/or FKS2-HS1 nucleic acid targets in a sample, wherein the method includes (a) combining in a chamber a sample comprising the plurality of nucleic acid targets, primer pairs for priming amplification of FKS1-HS1 and/or FKS2-HS1 nucleic acid targets, a labeling agent, and probes complementary to a plurality of FKS1-HS1 and/or FKS2-HS1 nucleic acid targets, wherein the probes are immobilized on a plurality of encoded magnetic beads such that the identity of each probe is known from the encoded magnetic bead on which it is immobilized (for example, each magnetic bead is uniquely labeled); (b) performing an amplification cycle, such as using asymmetric PCR, to form labeled amplification products from the FKS1-HS1 and/or FKS2-HS1 primer pairs; (c) hybridizing the labeled FKS1-HS1 and/or FKS2-HS1 amplification products to the FKS-HS1 and/or FKS2-HS1 probes immobilized on the encoded magnetic beads; (d) applying a magnetic field to a surface of the chamber to draw the encoded magnetic beads and the labeled amplification products hybridized to the probes immobilized on the encoded magnetic beads to the surface of the chamber; (e) detecting the encoded magnetic beads and the labeled amplification products. In some embodiments, the reaction products are quantitated.

In some embodiments, the methods also can include: (f) removing the magnetic field from the surface of the chamber prior to performing a further amplification cycle; and (g) repeating steps (b) through (f) at least once; wherein the plurality of nucleic acid targets in the sample are amplified and detected. In some embodiments, steps (b) through (f) are repeated between 10 to 40 times. In some embodiments, steps (b) through (f) are repeated at least 20 times. In some embodiments, the reaction products are quantitated.

In another embodiment, a method is provided for amplifying and detecting a the FKS1-HS1 and/or FKS2-HS1 nucleic acid target in a sample, wherein the method includes: (a) combining in a chamber a sample comprising the nucleic acid target, a primer pair for priming amplification of the FKS1-HS1 and/or FKS2-HS1 nucleic acid sequences, and a probe set complementary to the FKS1-HS1 and/or FKS2-HS1 target nucleic acid sequences, wherein the probe set comprises a first probe immobilized on a magnetic bead, and a second probe comprising a label; (b) performing an amplification cycle, such as asymmetric PCR, to form amplification products for the FKS1-HS1 and/or FKS2-HS1 nucleic acid target amplified with the primer pair; (c) hybridizing the amplification products to the probe set; (d) applying a magnetic field to a surface of the chamber to draw the magnetic bead and the amplification products hybridized to the probe immobilized on the encoded magnetic bead to the surface of the chamber; (e) detecting a signal from the second probe hybridized to the amplification products In some embodiments, the method also includes: (f) removing the magnetic field from the surface of the chamber prior to performing a further amplification cycle; and (g) repeating steps (b) through (f) at least once; wherein the nucleic acid target in the sample is amplified and detected. Different labels can be used on the second probes and/or by labeling or encoding the particles on which the first probes are immobilized. However, steps (f) and (g) need not be included in the assay.

General methods for preforming multiplex PCR reactions using particles are disclosed, for example, in U.S. Published Patent Application No. 2013/0116141, and U.S. Pat. No. 7,955,802, which are incorporated herein by reference. As disclosed in these patent publications, particles can be particles with magnetic properties and/or particles with a density that allows them to rest upon a two dimensional surface in solution. The particles can in one way or another rest upon a two dimensional surface by magnetic, gravitational, or ionic forces, or by chemical bonding, or by any other means known to those skilled in the art. Particles include glass, polystyrene, latex, metal, quantum dot, polymers, silica, metal oxides, ceramics, or any other substance suitable for binding to nucleic acids, or chemicals or proteins which can then attach to nucleic acids. The particles can be rod shaped or spherical or disc shaped, or comprise any other shape. The particles can be distinguishable by their shape, size and/or physical location. The particles may be spectrally distinct by virtue of having a composition containing dyes or ratios or concentrations of one or more dyes or fluorochromes, or may be distinguishable by barcode or holographic images or other imprinted forms of particle coding.

Where the particles are magnetic particles, they can be attracted to the surface of the chamber by application of a magnetic field. In addition, magnetic particles can be dispersed from the surface of the chamber by removal of the magnetic field. The magnetic particles can be paramagnetic or superparamagnetic. Paramagnetic and superparamagnetic particles have negligible magnetism in the absence of a magnetic field, but application of a magnetic field induces alignment of the magnetic domains in the particles, resulting in attraction of the particles to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field. Where the particles have a sufficient density they may be attracted to the bottom surface of the chamber by gravity, and dispersed from the bottom surface of the chamber by agitation of the chamber, such as by vortexing, sonication, or fluidic movement. Agitation of the chamber can also be used to assist in dispersing particles in methods and systems in which the particles were attracted to a surface of the chamber by other forces, such as magnetic or ionic forces, or suction forces, or vacuum filtration, or affinity, or hydrophilicity or hydrophobicity, or any combination thereof.

A labeling agent or label is a molecule that facilitates the detection of a molecule (e.g., a nucleic acid sequence) to which it is attached. Numerous labeling agents for nucleic acids are known. These include fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H benz[e]indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, ALEXA FLUOR® dyes, AMCA, BODIPY® 630/650, BODIPY® 650/665, BODIP®-FL, BODIPY®-R6G, BODIPY®-TMR, BODIPY®-TRX, CASCADE BLUE®, CYDYE™, including but not limited to CY2™, CY3™, and CY5™, a DNA intercalating dye, 6-FAM™, Fluorescein, HEX™, 6-JOE, OREGON GREEN® 488, OREGON GREEN® 500, OREGON GREEN® 514, PACIFIC BLUE®, REG, phycobilliproteins including, but not limited to, phycoerythrin and allophycocyanin, RHODAMINE GREEN™, RHODAMINE RED™, ROX™, TAMRA™, TET™, Tetramethylrhodamine, or TEXAS RED®. A signal amplification reagent, such as tyramide (PerkinElmer), can be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, can also be employed.

Labeled amplification products also can be labeled directly or indirectly. Direct labeling may be achieved by, for example, using labeled primers, using labeled dNTPs, using labeled nucleic acid intercalating agents, or combinations of the above. Indirect labeling may be achieved by, for example, hybridizing a labeled probe to the amplification product, or by using biotin label and then contacting the product with streptavidin linked to a label. In some examples, one of the amplification primers is labeled. In yet other example, one of the amplification primers is labeled with biotin, and streptavidin coupled to a label, such as a fluorescent label, is include in the reaction. In further examples, streptavidin coupled to phycoerythrin is added to the reaction and used to identify amplified DNA.

As disclosed herein, encoded particles, such as encoded magnetic beads, can be labeled with fluorescent dyes. Encoding with fluorescent dyes can employ fluorescent dyes with different fluorescent emission wavelengths and/or different fluorescent intensities. In some embodiments, the method can include determining a median fluorescent intensity (MFI) of the fluorescent signal from a plurality of the magnetic beads. Thus, the method can include determining the MFI of the fluorescent signal from about 50- to about 500 magnetic beads, such as about 50, 75, 100, 125, 15, 175, 200, 300, 400 or 500 of the magnetic beads. A high MFI indicates a strong binding of the probe to the target DNA. In contrast, a low MFI means the probe and the target DNA do not specifically bind. In one embodiment, a high MFI is greater than about 700. In other embodiments, a high MFI is greater than about 800, greater than about 900, or greater than about 1000. In additional embodiments, a high MFI is greater that about 1050, greater than about 1100, greater than about 1150, or greater than about 1200. In another embodiment, a low MFI is less than about 200. In yet other embodiments, a low MFI is less than bout 150 or less than about 100. In further embodiments, a low MFI is as less than about 95, less than about 90, less than about 85 or less than about 80. MFI can be determined by the MAGPIX® signal detection mechanism.

In additional embodiments, the method can include correlating the fluorescent signal with the amount the nucleic acid target in the sample. In some embodiments, this include: (a) plotting the signal against amplification cycle number; and (b) comparing the plot of the signal to the amplification cycle number to a standard curve produced by real-time PCR of serial dilutions of a known amount of the nucleic acid target. Thus, the method can include determining the MFI of magnetic beads that are encoded with fluorescent dyes having different emission wavelengths, different fluorescent intensities, or both. In some embodiments, the assay is a multiplex assay, such as the assays disclosed herein. In these embodiments, more than one MFI is determined.

The method can further include combining a negative control magnetic bead in the chamber. Thus, the method can include determining a MFI of the fluorescent signal from a plurality of the encoded magnetic beads, and determining a MFI of a fluorescent signal from a plurality of the negative control beads. In some examples, the method includes subtracting the MFI of the negative control beads from the MFI of the encoded magnetic beads.

The methods can include quantifying the initial amount of FKS1-HS1 and/or FKS2-HS1 nucleic acids in the sample. The quantification may comprise, for example, determining the relative concentrations of DNA present during the exponential phase of the real-time PCR by plotting fluorescence against cycle number on a logarithmic scale. The amounts of DNA may then be determined by comparing the results to a standard curve produced by real-time PCR of serial dilutions of a known amount of DNA.

Each amplification cycle has three phases: a denaturing phase, a primer annealing phase, and a primer extension phase. The amplification cycle can be repeated until the desired amount of amplification product is produced. Typically, the amplification cycle is repeated between about 10 to 40 times, such as such as 15 to 40 times, such as 20 to 40 times. The amplification cycle can be repeated, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29 or 40 times. For real-time PCR, detection of the amplification products will typically be done after each amplification cycle. In some embodiments, detection of the amplification products may be done after every second, third, fourth, or fifth amplification cycle. Detection may also be done such that as few as two or more amplification cycles are analyzed or detected.

As disclosed in published U.S. Patent Application No. 2011/0223602, incorporated herein by reference, the amplification cycle may be performed in the same chamber in which the detection of the amplification occurs. Thus, the chamber can include a heating element so the temperature in the chamber can be adjusted for the denaturing phase, primer annealing phase, and a primer extension phase of the amplification cycle. The heating element can be under the control of a processor. The amplification cycle can, however, be performed in a different chamber from the chamber in which detection of the amplification occurs. Thus, the "amplification" chamber can need to include a heating element but the "detection" or "imaging" chamber may not include a heating element. Where amplification and detection occur in separate chambers, the fluid in which the amplification reaction occurs may be transferred between the chambers by, for example, a pump or piston. The pump or piston may be under the control of a processor. Alternatively, the fluid can be transferred between the chambers manually using, for example, a pipette.

The chamber can be for example, a quartz chamber. A magnetic field may be applied to the chamber to attract magnetic particles within the chamber to a surface of the chamber by placing a permanent magnet adjacent to the surface of the chamber or by turning on an electromagnet adjacent to the surface of the chamber. The magnet need not be in physical contact with the chamber as long as it is close enough for its magnetic field to attract the magnetic particles within the chamber to the chamber surface. The magnetic field may be removed from the chamber by moving the permanent magnet away from the chamber or by turning off the electromagnetic. An electromagnet that is turned on can also be applied or removed from the chamber by moving closer or farther from the chamber as described above for a permanent magnet. In embodiments where the amplification and detection occur in the same chamber, the magnetic field may be applied during the primer annealing phase of the amplification cycle, during the primer extension phase of the amplification cycle, or following the amplification cycle. In embodiments, where the amplification and detection occur in different chambers, the magnetic field will typically be applied following the amplification cycle when the amplification reaction fluid is transferred into the detection chamber.

As disclosed in published U.S. Patent Application No. 2011/0223602, incorporated herein by reference, encoded particles and amplification products on the surface of the chamber can be detected using an imaging system. For example, detecting the encoded magnetic beads and the labeled amplification products can include imaging fluorescent wavelengths and/or fluorescent intensities emitted from the encoded magnetic beads and the labeled amplification products. The imaging may include taking a decoding image to identify the beads on the surface of the chamber and taking an assay imaging to detect amplification products on the surface of the chamber. A comparison of the decoding image and the assay image shows which beads have amplification products bound to them. Since the identities of the probes attached to the beads is known by encoding of the beads, the identity of the amplification product hybridized to the probe may also be determined. The methods can also include correlating the signal from the labeled amplification product with the concentration of FKS1-HS1 DNA or FKS2-HS1 DNA in the sample. This correlation can include determining the relative concentrations of DNA present during the exponential phase of real-time PCR by plotting fluorescence against cycle number on a logarithmic scale and comparing the results to a standard curve produced by real-time PCR of serial dilutions of a known amount of DNA.

This disclosure is illustrated by the following non-limiting Examples:

EXAMPLES

Echinocandins are the recommended treatment for invasive candidiasis due to *Candida glabrata*. Resistance to echinocandins is known to be caused by non-synonymous mutations in the hotspot-1 (HS1) regions of the FKS1 and FKS2 genes which encode a subunit of the β-1,3-glucan synthase, the target of the echinocandins. The development of a microsphere-based assay is disclosed below. This assay uses LUMINEX® MAGPIX® technology to identify mutations in the FKS1 and FKS2-HS1 domains which confer in vitro echinocandin resistance in *C. glabrata* isolates. The assay is rapid and can be performed with high throughput. The assay was validated using 102 isolates that had FKS1-HS1 and FKS2-HS1 domains previously characterized by DNA sequencing. The assay was 100% concordant with DNA sequencing results. The assay was then used for high throughput screening of 1032 *C. glabrata* surveillance isolates. Sixteen new isolates with mutations were identified, as well as a mutation new to our collection, del659F. This assay provides a rapid and cost-effective way to screen *C. glabrata* isolates for echinocandin resistance.

Example 1

Materials and Methods

*Candida glabrata* Culture and DNA Extraction.

All *C. glabrata* isolates employed in this study were obtained from patients diagnosed with candidemia as part of a population-based active surveillance program (Cleveland et al., 2012, Clinical Infectious Diseases. 55:1352-1361). Species were determined molecularly as previously described (Lockhart et al., 2012. J. Clin. Microbiol. 50:3435-3442).

Design of FKS Primers and Probes.

The hotspot-1 regions of both FKS1 and FKS2 genes were sequenced using the primer sets described by Zimbeck and colleagues (Zimbeck et al., 2010, Antimicrob Agents Chemother. 54(12):5042-7). Primers for the MagPix assay were designed using OLIGOPERFECT™ Designer, an online-based software provided by Life Technologies (tools_lifetechnologies_com/content.cfm?pageid=9716&icid=fr-oligo-6; New York, USA). The FKS1 hotspot1 region was amplified using the MgPxCgF1H1-F (5'-TCA AAC CTT CAC TGC CTC CT-3', SEQ ID NO: 15) and the BtMgPxCgF1H1-R (5'-TTT GAT TGA TGT CTA CAT AGC TTT-3', SEQ ID NO: 16) primer pair while the FKS2 hotspot1 region was amplified using the MgPxCgF2H1-1F (5'-TCT TTT GCC CCA TTA CAA GG-3', SEQ ID NO: 17) and the BtMgPxCgF2H1-R (5'-AAC CCC ACC AAT ACT CAC CA-3', SEQ ID NO: 18) primer pair. Both BtMgPxCgF1H1-R and BtMgPxCgF2H1-R were biotinylated at the 5' end. Guidelines from LUMINEX® Corporation (Austin, Tex.) were used for the design of all probes used for the detection of single nucleotide polymorphisms (SNPs) within the FKS1-HS1 and the FKS2-HS1. The design included coupling an amino group to the 5' end of the oligonucleotide by a 12-carbon spacer. The probes also were designed to complement the product of the biotinylated 'reverse' primers.

Crosslinking of FKS Probes to the Microspheres.

Carboxylated paramagnetic microspheres from LUMINEX® Corp were covalently linked to the specific probe as instructed by the manufacturer with minor modifications. The probe was titrated against a fixed number of microspheres in order to determine the appropriate amount of probe for the coupling process. The following conditions were used to cross-link the probes to the microspheres following determination of the optimal ratio of probe to microsphere. Approximately $5 \times 10^6$ of microspheres were transferred to a low-binding micro-centrifuge tube. The microsphere storage buffer was removed after 3 minutes of centrifugation at 6000×g. After decanting the microsphere storage buffer, 50 µl of 100 mM 2-(N-morpholino) ethanesulfonic acid (MES), 6 µl of 50 µM or 300 pmol amine-linked probe, and 10 µl of the 1-ethyl-3-(3-dimethylaminothe propyl) carbodiimide hydrochloride (EDC) catalyst were successively added to the microsphere pellet. The reaction was briefly mixed, covered, and incubated at 25° C. with constant shaking at 4000 rpm for 30 minutes. Then, a second addition of 10 µl of EDC followed by another round of 30 minutes incubation at 25° C. in the dark and with constant agitation at 4000 rpm. EDC was freshly prepared each time by dissolving EDC powder in sterile distilled-water to obtain a 10 mg/ml concentration solution. The reaction was terminated by adding 1 ml of 0.02% tween-20 followed by a brief vortex, 2 minutes of centrifugation at 6000×g, and removal of the supernatant. The microspheres were then washed once with 1 ml of 0.1% SDS. After a brief vortex and 2 minutes of centrifugation at 6000×g, the supernatant was aspirated and the coupled microspheres were re-suspended in 100 µl of TE.

FKS Hotspots Mutations Detection and Validation.

For the detection of SNPs within FKS1-HS1 and FKS2-HS1 regions, asymmetrical PCR primed by the hemi-biotinylated primer pairs was employed to amplify the hotspot regions and probed with the microsphere-conjugated probes described above. Asymmetrical PCR was conducted by combining 2 pmol of the forward and 16 pmol of the reverse PCR primers (1:8 ratio), 3 nmol of each dNTP (Roche, Switzerland), 0.9 µl of dimethyl sulfoxide, 3 µl of 10×PCR buffer with $MgCl_2$ (Roche), 0.15 U of Taq polymerase (Roche), 2 µl of DNA template, and sterile double-distilled water in a 30 µl reaction. In order to increase the throughput of this assay, PCR was carried out in a 96-well plate format. DNA amplification of the target regions was conducted with the following cycling conditions: 94° C. for 5 min; 40 cycles consisting of 94° C. for 30 s, 52° C. for 30 s, and 72° C. for 30 s; and a final extension at 72° C. for 2 min. PCR products were visualized by ethidium bromide gel electrophoresis prior to their hybridization with the microsphere-conjugated probes.

Hybridization of the probe to its target was accomplished as described (Etienne et al., 2009, J. Clin. Microbiol. 47(4): 1096-100) with minor modifications. For probe binding optimization, 10 µl of the PCR product, 7 µl of TE, and 33

µl of 1.5×TMAC buffer that contained ~3,960 of each microsphere-conjugated probe were mixed in a tube. For the high throughput screening of the *C. glabrata* collection, 17 µl of the PCR product was mixed with 33 µl of microsphere-conjugated probes in TMAC buffer. Each DNA mixture was subjected to denaturation by heating the reaction at 95° C. for 5 minutes and annealing for 30 minutes at 48° C. for FKS1 or 52° C. for FKS2. Immediately after the annealing step, the reaction mixture was centrifuged for 2 minutes at 1000×g and the supernatant was carefully removed without disturbing the microspheres. The hybrid DNA product was re-suspended in 75 µl of 1×TMAC buffer that contained 0.3 µg of Streptavidin-R-phycoerythrin (Life Technologies). The reaction was transferred to the MagPix system for signal acquisition.

Assay Signal Acquisition and Data Analysis. The signal generated by the interaction between the probe and its target was captured using the MAGPIX® system and xPONENT 4.2 software (LUMINEX®). Prior to signal acquisition, the reaction was incubated for 10 minutes at either 48° C. for FKS1 or 52° C. for FKS2. The fluorescent intensity of 50 microspheres per probe was captured by MAGPIX® to generate the median fluorescence intensity (MFI). All MAGPIX® assays containing unknown isolates were run with reference isolates and a no-template control. The FKS1-HS1 and FKS2-HS1 profile for a particular isolate was assigned according to the highest net MFI (probe signal-background signal) above 250. Data was considered unreliable if the net MFI for reference isolates were below 250.

Example 2

FKS Probes and Amplicons

For FKS1-HS1, four unique probes to detect the three non-synonymous mutations at T1885C (CgMgPxF1H1-S629P), A1891G (CgMgPxF1H1-R631G), and A1895T (CgMgPxF1H1-D632V) as well as the synonymous mutation at C1875T (CgMgPxF1H1-SmT) were designed (FIG. 1). Two probes, CgMgPxF1H1-SmC and CgMgPxF1H1-WT1, were created to detect wild type FKS1-HS1. All FKS1-HS1 probes contain only one SNP that corresponds to each mutation except for FKS1-D632V; there was a lower nonspecific signal when the last nucleotide was changed from an adenosine to a thymidine. The G-C content for FKS1-HS1 probes is between 25-36.8% with a melting temperature (Tm) between 47.7-51.8° C. and an average Tm of 50° C.

Nine different probes to detect the wild type copy and the mutant copies of FKS2-HS1 were constructed (FIG. 2). For FKS2-HS1, the domain was divided into two parts at the 12$^{th}$ nucleotide of the domain. The three probes that cover the first part of the FKS2-HS1 domain are CgMgPxF2H1-F659S, CgMgPxF2H1-F659Y, and their wild type counterpart, CgMgPxF2H1-WT1. These probes cover nine nucleotides upstream as well as the first 11 nucleotides of the domain. The probes within the second part of the domain are CgMgPxF2H1-R665G, CgMgPxF2H1-D666V, CgMgPxF2H1-P667H, and their wild type counterpart, CgMgPxF2H1-WT2. These probes encompass the last 15 nucleotides. The third set of probes, CgMgPxF2H1-S663P and CgMgPxF2H1-S663F, stretch from the fourth to the 23rd nucleotide. All FKS2-HS1 probes contain only one SNP and their G-C composition is between 25-47.4%. The Tm for FKS2-HS1 probes is between 51.2-57.2° C., with an average Tm of 53.4° C.

The targets for the FKS probes were generated using asymmetrical PCR. The selected FKS1-HS1 and FKS2-HS1 primer sets in the assay generate PCR-product sizes of 213 and 172 nucleotides, respectively. Cross-amplification of the two FKS genes for these two primer sets was not observed. The interaction between the probe and the target is also dependent on the availability of the target. A number of forward to reverse primer ratios were tested and the 1 to 8 primer ratio gave the best signal and was chosen for the assay.

Example 3

FKS Probes Demonstrated Discriminatory Affinity for their Targets

A goal of the project was to design capture probes for a multiplex assay that would allow the rapid detection of SNPs that are known to confer resistance to one or more echinocandins. The probes' affinity for their targets was determined by using a panel of reference isolates with known FKS mutations. The FKS1-HS1 probes, were tested against four isolates in which an FKS1-HS1 mutation had been identified by DNA sequencing. The probes each showed specific affinity for their preferential target when hybridized at 48° C. (Table 1).

TABLE 1

Capture probes.*

FKS1-HS1 and FKS2-HS1 Capture Probes

| Probe Name | Probe Sequence | nt | G-C% | Tm° C. |
|---|---|---|---|---|
| MgPxCgF1H1-WT1 | TCTATCTCTAAGAGATCCAAT | 21 | 33.3 | 51.8 |
| MgPxCgF1H1-SmC | GAATCATACTACTT<u>C</u>TTGAT | 20 | 30.0 | 47.7 |
| MgPxCgF1H1-SmT | GAATCATACTACTT<u>T</u>TTGAT | 20 | 25.0 | 48.0 |
| MgPxCgF1H1-S629P | TTGATTCTA<u>C</u>CTCTAAGAGA | 20 | 35.0 | 51.2 |
| MgPxCgF1H1-R631G | TATCTCTA<u>G</u>GAGATCCAAT | 19 | 36.8 | 50.6 |
| MgPxCgF1H1-D632V | TCTATCTCTAAGAG<u>T</u>TCCAT | 20 | 35.0 | 50.1 |
| MgPxCgF2H1-WT1 | TCGTACTTCTTCTTGATTTT | 20 | 30.0 | 53.8 |
| MgPxCgF2H1-F659Y | TCGTACTTCT<u>A</u>CTTGATTTT | 20 | 30.0 | 51.3 |
| MgPxCgF2H1-F659S | TCGTACTTCT<u>C</u>CTTGATTTT | 20 | 35.0 | 56.1 |
| MgPxCgF2H1-S663P | TTGATTTTG<u>C</u>CTCTAAGAGA | 20 | 35.0 | 57.2 |
| MgPxCgF2H1-S663F | TTGATTTTGT<u>TT</u>TCTAAGAGA | 20 | 25.0 | 52.2 |
| MgPxCgF2H1-R665G | TCTCTA<u>G</u>GAGACCCTATCA | 19 | 47.4 | 54.3 |
| MgPxCgF2H1-D666V | TCTCTAAGAG<u>T</u>CCCTATCAG | 20 | 45.0 | 53.2 |
| MgPxCgF2H1-P667H | TCTCTAAGAGACC<u>A</u>TATCAG | 20 | 40.0 | 51.4 |
| MgPxCgF2H1-WT2 | TCTCTAAGAGACCCTATCA | 19 | 42.1 | 51.7 |

*These probes are also shown in Fig. 1 and Fig. 2. For F1H1, WT1 is SEQ ID NO: 19, SmC is SEQ ID NO: 3, SmT is SEQ ID NO: 4, 629P is SEQ ID NO: 5, 631G is SEQ ID NO: 6, and 632V is SEQ ID NO: 7. For F2H1, WT1 is SEQ ID NO: 20, 659Y is SEQ ID NO: 8, 659S is SEQ ID NO: 9, 663P is SEQ ID NO: 10, 663F is SEQ ID NO: 11, 665G is SEQ ID NO: 12, 666V is SEQ ID NO: 13, 667H is SEQ ID NO: 14, and WT2 is SEQ ID NO: 21.
Probe properties were assessed using Multiple primer analyzer from Thermo Scientific (http://thermoscientificbio.com/webtools/multipleprimer/).

The CgMgPxF1H1-SmT probe displayed the highest average MFI at 5342±106 while the CgMgPxF1H1-R631G showed the lowest average MFI at 771±83 for their respective targets. All of the SNP probes displayed at least 100-fold higher specific signal than non-specific signal. Both wild type probes showed some affinity to the SNP targets, though significantly lower than to the wild type targets. The FKS1-HS1 probes were also tested against 28 different products of FKS2-HS1 with or without mutations. The average MFI for any probes against FKS2-HS1 target was less than 200, which is in the negligible range.

tested against 28 different targets of FKS1-HS1 with or without mutations. They showed no affinity for the FKS1-HS1 domain products.

Example 4

FKS SNP Detection Validation and High Throughput Screening

After the binding affinity for the probes and the parameters for the MAGPIX® assay were established, the assay

TABLE 2

MFI values for each of the probes used for FKS1-HS1. Values represent three replicates with the value against the correctly corresponding sequence in bold.

| C. glabrata isolate | MgPxCgF1H1-SmC | MgPxCgF1H1-SmT | MgPxCgF1H1-WT1 | MgPxCgF1H1-S629P | MgPxCgF1H1-R631G2 | MgPxCgF1H1-D632V |
|---|---|---|---|---|---|---|
| | Average MFI with standard error for FKS1-HS1 probes | | | | | |
| Reference-WT | 2487 ± 367 | 379 ± 75 | 1081 ± 207 | (−)22 ± 2 | (−)8 ± 11 | 49 ± 12 |
| Reference-S629P | 1245 ± 72 | 5342 ± 106 | 1538 ± 15 | 3095 ± 133 | (−)7 ± 11 | (−)30 ± 15 |
| Reference-R631G | 2669 ± 91 | 360 ± 42 | 64 ± 24 | (−)25 ± 24 | 771 ± 83 | (−)27 ± 23 |
| Reference-D632V | 1077 ± 406 | 4545 ± 1123 | 845 ± 342 | 22 ± 19 | (−)5 ± 6 | 3736 ± 691 |

TABLE 3

MFI values for each of the probes used for FKS2-HS1. Values represent three replicates with the value against the correctly corresponding sequence in bold.

| Isolate mutation | MgPxCgF2H1-WT1 | MgPxCgF2H1-F659Y | MgPxCgF2H1-F659S | MgPxCgF2H1-S663P | MgPxCgF2H1-S663F |
|---|---|---|---|---|---|
| | Average MFI with standard error | | | | |
| RefFKS2-WT | 4899 ± 1354 | 1385 ± 721 | 841 ± 497 | (−)20 ± 12 | (−)78 ± 20 |
| RefFKS2-F659Y | 1054 ± 308 | 3673 ± 494 | 259 ± 88 | 17 ± 25 | (−)60 ± 20 |
| RefFKS2-F659S | 1120 ± 470 | 1750 ± 534 | 4151 ± 654 | (−)32 ± 9 | (−)82 ± 6 |
| RefFKS2-S663P | 5189 ± 987 | 1098 ± 418 | 689 ± 310 | 3391 ± 741 | (−)94 ± 9 |
| RefFKS2-S663F | 5437 ± 511 | 1045 ± 275 | 695 ± 241 | (−)51 ± 14 | 3071 ± 287 |
| RefFKS2-R665G | 5024 ± 1221 | 1211 ± 506 | 693 ± 320 | (−)67 ± 9 | (−)124 ± 10 |
| RefFKS2 D665V | 3950 ± 66 | 635 ± 82 | 256 ± 36 | 111 ± 29 | 89 ± 38 |
| RefFKS2-P665H | 2630 ± 453 | 261 ± 122 | 33 ± 29 | (−)30 ± 7 | (−)105 ± 9 |

| Isolate mutation | MgPxCgF2H1-R665G | MgPxCgF2H1-D666V | MgPxCgF2H1-P667H | MgPxCgF2H1-WT2 |
|---|---|---|---|---|
| | Average MFI with standard error | | | |
| RefFKS2-WT | (−)97 ± 41 | 46 ± 101 | 108 ± 120 | 1209 ± 603 |
| RefFKS2-F659Y | (−)99 ± 36 | 61 ± 41 | 107 ± 45 | 1069 ± 374 |
| RefFKS2-F659S | (−)95 ± 36 | 34 ± 91 | 94 ± 108 | 1091 ± 470 |
| RefFKS2-S663P | (−)47 ± 27 | 232 ± 108 | 378 ± 182 | 2365 ± 694 |
| RefFKS2-S663F | (−)86 ± 79 | 92 ± 97 | 164 ± 97 | 1782 ± 402 |
| RefFKS2-R665G | 778 ± 374 | (−)132 ± 4 | (−)121 ± 19 | 170 ± 117 |
| RefFKS2 D665V | (−)158 ± 37 | 3938 ± 157 | (−)86 ± 10 | 50 ± 25 |
| RefFKS2-P665H | (−)201 ± 58 | (−)144 ± 45 | 1359 ± 366 | (−)158 ± 37 |

The FKS2-HS1 probes were tested against eight isolates in which an FKS2-HS1 mutation had been identified by DNA sequencing. Each of the probes showed preferential and robust affinity for their target when hybridized at 52° C. The CgMgPxF2H1-WT1 probe displayed highest average MFI at 5437±511 while the CgMgPxF2H1-R665G showed the lowest average MFI at 778±374 for their respective target. The CgMgPxF2H1-S663P/F, -R665G, and -D666V probes displayed at least 100-fold higher specific signal than non-specific signal while the other probes showed at least 2.5-fold higher signal. The FKS2-HS1 probes were also was used to screen a collection of C. glabrata isolates for mutations in the hotspot 1 regions of FKS1 and FKS2. The assay was first validated by testing all the isolates for which both FKS1-HS1 and FKS2-HS1 had been previously sequenced (102 isolates; 70 wild-type, 5 S629P, 3 R631G, 1 R631G and D666V double-mutant, 1 D632V, 2 F659Y, 1 F659S, 15 S663P, 2 S663F, 1 R665G, and 1 P667H). The MAGPIX® assay results were 100% concordant with the DNA sequencing profile of these 102 isolates. All of the mutations were correctly identified and all of the wild-type isolates were identified as wild-type.

Following validation, high throughput screening was initiated of an additional collection of 1032 *C. glabrata* isolates from the surveillance study. The screen identified eleven additional isolates with non-synonymous mutations (2 S629P/D666V double-mutants, 3 F659Y, and 6 S663P) in either FKS1-HS1 or FKS2-HS1. In addition, five isolates displayed an irregular FKS2-HS1 probe signal-pattern. Because wild-type probes were included with each screen, the assay was able to facilitate the discovery of three isolates with the del659F mutation, a deletion of the phenylalanine adjacent to the phenylalanine at the beginning of FKS2-HS1. This mutation was not included in the original assay but does confer echinocandin resistance (Alexander et al., 2013, Clin Infect Dis. 56(12):1724-32; Garcia-Effron, 2009, Antimicrob Agents Chemother. 53(9):3690-9). The other two isolates had the S663P mutation in addition to a silent mutation at G1986A. All of the mutations identified by the MAGPIX® assay were confirmed to be present by DNA sequencing of the corresponding region.

Thus, an assay has been developed for rapid and high-throughput identification of SNPs in FKS1 or FKS2 of *C. glabrata*. Two sets of probes were constructed for the detection of SNPs in FKS1-HS1 and FKS2-HS1. All probes showed adequate discriminatory binding for their respective target, but probes with the SNPs located at or near the ends of the probe showed some cross-binding. An example is CgMgPxF1H1-WT1 which showed strong binding to both the S629P and D632V targets because both SNPs are located five to six nucleotides from the end of that probe. Likewise, CgMgPxF2H1-WT2 showed affinity for the S663P/S663F targets because these SNPs are located within the last two nucleotides of that probe. However, the predictive power for these probes improved considerably when they were pooled because the difference in binding was significant. For the FKS1-HS1 probe set, the specific MFI signal was at least twice the highest non-specific signal for any target. This is also true for the FKS2-HS1 probe set and their targets, with the exception of the probe for the most common mutation, S663P. The specific MFI signal is at least 0.5-fold higher than the highest non-specific signal (CgMgPxF2H1-WT2), and in every case was higher than the wild-type signal. Additionally, neither probe set showed any cross-affinity for heterologous targets; the two HS domains share very high sequence identity at both the nucleotide and amino acid level.

Without being bound by theory, an important parameter of the assay is the MFI. The MFI is dependent upon the interaction between the probe and the target. Several factors affect this interaction. First, the abundance and availability of the target is essential to achieve a high MFI. This was optimized by asymmetrical PCR. The probes complement the biotinylated PCR product so 8-fold more biotinylated primer than the non-biotinylated primer was used. This generated more single-stranded target for the probe to bind. The second factor that affects the MFI is probe accessibility. Therefore, it was essential to determine the optimal probe-to-microsphere ratio when conjugating the probes to the microspheres. The ratio of ~3 pmol of probe per 50,000 microspheres gave the best signal. In addition to target and probe quantity, the length of the target and the nucleotide composition of the probe also affect MFI. For FKS1-HS1, three different amplicons were tested before one was found that would give an adequate MFI signal for all FKS1-HS1 probes. In addition, the G-C content of the probe greatly affects the MFI. This observation becomes more apparent when comparing the MFI of CgMgPxF1H1-SmC to CgMgPxF1H1-SmT or CgMgPxF2H1-R665G to CgMgPxF2H1-WT2. The MFI for CgMgPxF1H1-SmC and CgMgPxF2H1-R665G are lower than for their counterpart probes because they both have a higher G-C content. This would explain why CgMgPxF2H1-R631G and CgMgPxF2H1-R665G displayed the lowest MFI. Lastly, the probe-target hybridization temperature was optimized. High hybridization temperature tends to decrease MFI while low hybridization temperatures decrease the signal-to-noise ratio. The optimal hybridization temperatures for FKS1-HS1 and FKS2-HS1 probes were 48° C. and 52° C., respectively, about 1-2 degrees below their average Tm.

The multiplex FKS-MAGPIX® assay developed here was highly accurate. The assay correctly identified all 102 isolates in which the profiles for both HS1 domains were known and was 100% concordant with DNA sequencing. This assay could be an alternative to sequencing for those labs which already have the LUMINEX® technology. Using this assay, the mutational profile to both FKS1 and FKS2-HS1 for 1032 isolates was derived in only a matter of days. From a *C. glabrata* collection, five mutant isolates were identified that were subsequently shown to have elevated echinocandin MIC values.

This assay can only identify known mutations in FKS1-HS1 and FKS2-HS1. For example, the assay poorly identified two isolates in which the FKS2-HS1 contained a previously unknown silent mutation juxtaposed to the S663P mutation. To alleviate this problem, two sets of wild type probes, separated along the target region, were included in each assay. If there was an unknown mutation, the signal for one of the wild-type probes would remain high while the other would drop. An unknown mutation was identified based on the signal pattern generated by the inclusion of multiple wild-type probes. Although the probes were not optimized to detect the del659F mutation (Alexander et al., 2013, Clin Infect Dis. 56(12):1724-32; Garcia-Effron et al., 2009, Antimicrob Agents Chemother. 53(9):3690-9), it was identified by analyzing the CgMgPxF2H1-WT1 and CgMgPxF2H1-WT2 signal ratio. The CgMgPxF2H1-WT1 signal was typically at least 2-fold higher than that of CgMgPxF2H1-WT2. However, for the del659F mutant, the signal was reversed for these two probes. In subsequent sequencing of the FKS genes of *C. glabrata* isolates with elevated echinocandin MICs, no mutations were detected in HS2, therefore it was not included in this assay. Although these new mutations were not identified by the assay, the isolates were identified as non-wild-type.

The multiplex FKS-MAGPIX® assay is rapid and highly versatile. The FKS1-HS1 and FKS2-HS1 profiles of up to 95 isolates can be determined in as little as five hours. Unlike DNA sequencing, MAGPIX® data was easy to analyze and allele profiles could easily be assigned. The assay is highly adaptable to low or high throughput format. New mutations can easily be incorporated into the existing assay although some optimization would be necessary. This assay was designed for and can be used to detect echinocandin resistance in *C. glabrata* isolates very rapidly, and can be used for early therapy decisions.

Pham et al., "Development of a LUMINEX®-based multiplex assay for detection of mutations conferring resistance to echinocandins in *Candida glabrata*," J. Clin. Microbiol. 52(3): 1-6, 2014 is incorporated herein by reference.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for detecting a *C. glabrata* resistant to an echinocandin in a sample, comprising contacting a biological sample comprising DNA with unequal amounts of a forward primer and a reverse primer that can be used to amplify a FKS1-hot spot 1 (HS1) nucleic acid and unequal amounts of a forward and a reverse primer that can be used to amplify a FKS2-HS1 nucleic acid;

performing asymmetric polymerase chain reaction (PCR) to form amplified DNA product; and contacting the amplified DNA product with a set of probes, wherein each probe in the set of probes specifically binds FKS1-HS1 DNA mutation or specifically binds a FKS2-HS1 DNA mutation, wherein each of the probes is labeled with a unique label such that the identity of each probe is known by detecting the label;

detecting amplified DNA product hybridized to the set of probes; and determining if a probe in the set of probes specific for the FKS1-HS1 DNA mutation or a probe in the set of probe specific for an FKS2-HS1 DNA mutation is bound to the amplified DNA product, wherein binding of the probe specific for the FKS1-HS1 DNA or the probe specific for an FKS2-HS1 DNA mutation indicates that the *C. glabrata* is resistant to the echinocandin is present in the sample.

2. The method of claim 1, wherein the method further comprises contacting the amplified DNA product with a probe that specifically binds a FKS1-HS1 wild type nucleic acid comprising the nucleic acid sequence set forth as SEQ ID NO: 19.

3. The method of claim 1, wherein the method further comprises contacting the amplified DNA product with a probe that specifically binds a FKS2-HS1 wild type nucleic acid comprising the nucleic acid sequence set forth as SEQ ID NO: 20 or SEQ ID NO: 21.

4. The method of claim 1, wherein the set of probes specific for the FKS1-HS1 mutation comprises:

a) a probe that specifically binds FKS1-HS1 encoding FKS1 with a 629P mutation;

b) a probe that specifically binds FKS1-HS1 encoding FKS1 with a 631G mutation; and c) a probe that specifically binds FKS1-HS1 encoding FKS1 with a 632V mutation, wherein each capture probe in labeled with a unique detectable label.

5. The method of claim 4, wherein:

a) the probe that specifically binds FKS1-HS1 encoding FKS1 with a 629P mutation comprises the nucleic acid sequence set forth as SEQ ID NO: 5;

b) the probe that specifically binds FKS1-HS1 encoding FKS1 with a 631G mutation comprises the nucleic acid sequence set forth as SEQ ID NO: 6; and c) the probe that specifically binds FKS1-HS1 encoding FKS1 with a 632V mutation comprises the nucleic acid sequence set forth as SEQ ID NO: 7.

6. The method of claim 1, wherein the method further comprises contacting the amplified DNA product with a) a probe that specifically binds FKS1-HS1 DNA encoding FKS1 with a smC mutation; and/or b) a probe that specifically binds FKS1-HS1 encoding FKS1 with a smT mutation.

7. The method of claim 6, wherein:

a) the probe that specifically binds FKS1-HS1 DNA encoding FKS1 with a smC mutation comprises the nucleic acid sequence set forth as SEQ ID NO: 3; and/or b) the probe that specifically binds FKS1-HS1 encoding FKS1 with a smT mutation comprises the nucleic acid sequence set forth as SEQ ID NO: 4.

8. The method of claim 1, wherein the set of probes specific for the FKS2-HS1 mutation comprises:
   a) a probe that specifically binds FKS2-HS1 DNA encoding FKS2 with a 659Y mutation;
   b) a probe that specifically binds FKS2-HS1 encoding FKS2 with a 659S mutation;
   c) a probe that specifically binds FKS2-HS1 encoding FKS2 with a 663P mutation;
   d) a probe that specifically binds FKS2-HS1 encoding FKS2 with a 663F mutation;
   e) a probe that specifically binds FKS2-HS1 encoding FKS2 with a 665G mutation;
   f) a probe that specifically binds FKS2-HS1 encoding FKS2 with a 666V mutation; and
   g) a probe that specifically binds FKS2-HS1 encoding FKS2 with a 667H mutation.

9. The method of claim 6, wherein:
   a) the probe that specifically binds FKS2-HS1 DNA encoding FKS1 with a 659Y mutation comprises the nucleic acid sequence set forth as SEQ ID NO: 8;
   b) the probe that specifically binds FKS2-HS1 encoding FKS1 with a 659S mutation comprises the nucleic acid sequence set forth as SEQ ID NO: 9;
   c) a probe that specifically binds FKS2-HS1 encoding FKS1 with a 663P mutation comprises the nucleic acid sequence set forth as SEQ ID NO: 10;
   d) a probe that specifically binds FKS2-HS1 encoding FKS1 with a 663P mutation comprises the nucleic acid sequence set forth as SEQ ID NO: 11;
   e) a probe that specifically binds FKS2-HS1 encoding FKS1 with a 665G mutation comprises the nucleic acid sequence set forth as SEQ ID NO: 12;
   f) a probe that specifically binds FKS2-HS1 encoding FKS1 with a 666V mutation comprises the nucleic acid sequence set forth as SEQ ID NO: 13; and
   g) a probe that specifically binds FKS2-HS1 encoding FKS1 with a 667H mutation comprises the nucleic acid sequence set forth as SEQ ID NO: 14.

10. The method of claim 1, wherein the forward primer that can be used to amplify a FKS1-HS1 nucleic acid comprises the nucleic acid sequence set forth as SEQ ID NO: 15, and the reverse primer that can be used to amplify a FKS1-HS1 nucleic acid comprises the nucleic acid sequence set forth as SEQ ID NO: 16.

11. The method of claim 10, wherein either the forward primer that can be used to amplify a FKS1-HS1 nucleic acid or the reverse primer that can be used to amplify the FKS1-HS1 nucleic acid is labeled.

12. The method of claim 11, wherein the label is biotin.

13. The method of claim 12, further comprising
   contacting the amplified DNA product with streptavidin coupled to a unique label, and
   detecting the unique label, wherein detection of the label indicates the presence of FKS1-HS1 amplified DNA.

14. The method of claim 1, wherein the forward primer that can be used to amplify a FKS2-HS1 nucleic acid comprise the nucleic acid sequence set forth as SEQ ID NO: 17, and the reverse primer that can be used to amplify a FKS2-HS1 nucleic acid comprise the nucleic acid sequence set forth as SEQ ID NO: 18.

15. The method of claim 14, wherein either the forward primer that can be used to amplify a FKS2-HS1 nucleic acid or the reverse primer that can be used to amplify the FKS2-HS1 nucleic acid is labeled with a unique label.

16. The method of claim 15, wherein the label is biotin.

17. The method of claim 16, further comprising
   contacting the amplified DNA product with streptavidin coupled to a unique label, and
   detecting the unique label, wherein detection of the label indicates the presence of amplified FKS2-HS1 DNA.

18. The method of claim 2, wherein the probe specific for wild-type FKS1-HS1 DNA is labeled with a unique label.

19. The method of claim 18, wherein the probe specific for wild-type FKS1-HS1 DNA comprises the nucleic acid sequence set forth as SEQ ID NO: 19.

20. The method of claim 3, wherein the probe specific for wild-type FKS2-HS1 DNA is labeled with a unique label.

21. The method of claim 20, wherein the probe specific for wild-type FKS2-HS1 DNA comprises the nucleic acid sequence set forth as SEQ ID NO: 20.

22. The method of claim 20, further comprising contacting the amplified DNA product with a second probe specific for wild-type FKS2-HS1 DNA labeled with a unique label.

23. The method of claim 22, wherein the second probe specific for wild-type FKS2-HS1 DNA comprises the nucleic acid sequence set forth as SEQ ID NO: 21.

24. The method of claim 1, wherein performing asymmetric PCR comprises performing quantitative PCR.

25. The method of claim 1, wherein each of the probes in the set of probes specific for the FKS1-HS1 mutation and each of the probes in the set of probes specific for the FKS1-HS2 mutation is also labeled with a magnetic label.

* * * * *

UNITED STATES PATENT AND TRADEMARK OFFICE
CERTIFICATE OF CORRECTION

Page 1 of 1

PATENT NO. : 9,920,385 B2
APPLICATION NO. : 14/875599
DATED : March 20, 2018
INVENTOR(S) : Pham et al.

It is certified that error appears in the above-identified patent and that said Letters Patent is hereby corrected as shown below:

On the Title Page

In the Abstract, "Method are also disclosed that utilize these probes and primers, wherein the methods can be used to detect a *C. glabrata* resistant to an echinocandin in a sample" should read -- Methods are also disclosed that utilize these probes and primers, wherein the methods can be used to detect a *C. glabrata* resistant to an echinocandin in a sample --

In the Claims

Claim 4, Column 40, Line 42, "probe in labeled with a unique detectable label." should read -- probe is labeled with a unique detectable label. --

Signed and Sealed this
Twentieth Day of April, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 22

<210> SEQ ID NO 1
<211> LENGTH: 214
<212> TYPE: DNA
<213> ORGANISM: Candida glabrata

<400> SEQUENCE: 1
ctcaaacctt cactgcctcc tttgcacctt tgcatggtct tgacagatgg ttgtcttacc    60
tggtttgggt tactgttttt gctgctaagt acgctgaatc atactacttc ttgattctat   120
ctctaagaga tccaatcaga attttgtcta ccactaccat gagatgtact ggtgaatact   180
ggtggggttc aaagctatgt agacatcaat caaa                               214

<210> SEQ ID NO 2
<211> LENGTH: 173
<212> TYPE: DNA
<213> ORGANISM: Candida glabrata

<400> SEQUENCE: 2
atcttttgcc ccattacaag gtttggatag atggttatct tatttagttt gggttacagt    60
ttttgctgcc aaatactctg aatcgtactt cttcttgatt ttgtctctaa gagaccctat   120
cagaatttta tcaactacta ccatgagatg tactggtgag tattggtggg gtt          173

<210> SEQ ID NO 3
<211> LENGTH: 20
<212> TYPE: DNA
<213> ORGANISM: Artificial Sequence
<220> FEATURE:
<223> OTHER INFORMATION: Probe

<400> SEQUENCE: 3
gaatcatact acttcttgat                                                20

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
gaatcatact acttttttgat                                               20

<210> SEQ ID NO 5
<211> LENGTH: 20
<212> TYPE: DNA
<213> ORGANISM: Artificial Sequence
<220> FEATURE:
<223> OTHER INFORMATION: Probe

<400> SEQUENCE: 5
ttgattctac ctctaagaga                                                20

<210> SEQ ID NO 6
<211> LENGTH: 19
<212> TYPE: DNA
<213> ORGANISM: Artificial Sequence
<220> FEATURE:
<223> OTHER INFORMATION: Probe

<400> SEQUENCE: 6
tatctctagg agatccaat                                                 19

```
<210> SEQ ID NO 7
<211> LENGTH: 17
<212> TYPE: DNA
<213> ORGANISM: Artificial Sequence
<220> FEATURE:
<223> OTHER INFORMATION: Probe

<400> SEQUENCE: 7
atctctaaga gttccat                                                  17

<210> SEQ ID NO 8
<211> LENGTH: 20
<212> TYPE: DNA
<213> ORGANISM: Artificial Sequence
<220> FEATURE:
<223> OTHER INFORMATION: Probe

<400> SEQUENCE: 8
tcgtacttct acttgatttt                                               20

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
tcgtacttct ccttgatttt                                               20

<210> SEQ ID NO 10
<211> LENGTH: 20
<212> TYPE: DNA
<213> ORGANISM: Artificial Sequence
<220> FEATURE:
<223> OTHER INFORMATION: Probe

<400> SEQUENCE: 10
ttgattttgc ctctaagaga                                               20

<210> SEQ ID NO 11
<211> LENGTH: 20
<212> TYPE: DNA
<213> ORGANISM: Artificial Sequence
<220> FEATURE:
<223> OTHER INFORMATION: Probe

<400> SEQUENCE: 11
ttgattttgt ttctaagaga                                               20

<210> SEQ ID NO 12
<211> LENGTH: 19
<212> TYPE: DNA
<213> ORGANISM: Artificial Sequence
<220> FEATURE:
<223> OTHER INFORMATION: Probe

<400> SEQUENCE: 12
tctctaggag accctatca                                                19

<210> SEQ ID NO 13
<211> LENGTH: 20
<212> TYPE: DNA
<213> ORGANISM: Artificial Sequence
<220> FEATURE:
```

<223> OTHER INFORMATION: Probe

<400> SEQUENCE: 13
tctctaagag tccctatcag                                       20

<210> SEQ ID NO 14
<211> LENGTH: 20
<212> TYPE: DNA
<213> ORGANISM: Artificial Sequence
<220> FEATURE:
<223> OTHER INFORMATION: Probe

<400> SEQUENCE: 14
tctctaagag accatatcag                                       20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tcaaaccttc actgcctcct                                       20

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
tttgattgat gtctacatag cttt                                  24

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tcttttgccc cattacaagg                                       20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
aaccccacca atactcacca                                       20

<210> SEQ ID NO 19
<211> LENGTH: 21
<212> TYPE: DNA
<213> ORGANISM: Artificial Sequence
<220> FEATURE:
<223> OTHER INFORMATION: Probe

<400> SEQUENCE: 19
tctatctcta agagatccaa t                                     21

```
<210> SEQ ID NO 20
<211> LENGTH: 20
<212> TYPE: DNA
<213> ORGANISM: Artificial Sequence
<220> FEATURE:
<223> OTHER INFORMATION: Probe

<400> SEQUENCE: 20
tcgtacttct tcttgatttt                                               20

<210> SEQ ID NO 21
<211> LENGTH: 19
<212> TYPE: DNA
<213> ORGANISM: Artificial Sequence
<220> FEATURE:
<223> OTHER INFORMATION: Probe

<400> SEQUENCE: 21
tctctaagag accctatca                                                19

<210> SEQ ID NO 22
<211> LENGTH: 9
<212> TYPE: PRT
<213> ORGANISM: Candida glabrata

<400> SEQUENCE: 22

Phe Leu Ile Leu Ser Leu Arg Asp Pro
1               5
```